United States Patent
Takayanagi et al.

(10) Patent No.: US 6,933,309 B2
(45) Date of Patent: Aug. 23, 2005

(54) HALOGENOBENZYL AMINOPROPIONIC ACID DERIVATIVES

(75) Inventors: Koichi Takayanagi, Saitama (JP); Hideki Yamada, Saitama (JP); Shin-ichi Kazayama, Saitama (JP); Shin-ya Ohnuma, Saitama (JP)

(73) Assignee: Toaeiyo Ltd., Tokyo (JP)

( * ) Notice: Subject to any disclaimer, the term of this patent is extended or adjusted under 35 U.S.C. 154(b) by 0 days.

(21) Appl. No.: 10/472,485

(22) PCT Filed: Dec. 26, 2002

(86) PCT No.: PCT/JP02/13573
§ 371 (c)(1),
(2), (4) Date: Sep. 29, 2003

(87) PCT Pub. No.: WO03/059895
PCT Pub. Date: Jul. 24, 2003

(65) Prior Publication Data
US 2004/0102439 A1 May 27, 2004

(30) Foreign Application Priority Data
Jan. 17, 2002 (JP) ........................................ 2002-008883

(51) Int. Cl.[7] .................. A61K 31/42; C07D 277/28
(52) U.S. Cl. .................. 514/375; 548/205; 548/236
(58) Field of Search .................. 548/205, 236; 514/375

(56) References Cited

FOREIGN PATENT DOCUMENTS

| WO | 96/38415 | 12/1996 |
| WO | 97/31907 | 9/1997 |
| WO | 00/08002 | 2/2000 |

OTHER PUBLICATIONS

Diabetes Care (US), American Diabetes Association, vol. 21, pp. 641–648 1998.
The Lancet (UK), Lancet, vol. 357, pp. 905–910 2001.

Kahn et al. DIABETOLOGY (DE), European Association for Study of Diabetes, vol. 39 (suppl), p. A53 1996.

G. Riccardi et al., "Effects of bezafibrate on insulin secretion and peripheral insulin sensitivity in hyperlipidemic patients with and without diabetes," *Atherosclerosis*, 75 (1989), Elsevier Scientific Publishers Ireland, Ltd., pp. 175–181.

G. Paragh et al., "Treatment Possibility of Hypercholesterolaemia Associated with Hypertriglyceridaemia," *Acta Biologica Hungarica* 48 (3) (1997), pp. 359–367.

M. Yoshinari et al., "Effect of gemfibrozil on serum levels of prostacycin and precursor fatty acids in hyperlipidemic patients with Type 2 diabetes," Diabetes Research and Clinical Practice 42 (1998), pp. 149–154.

Y. Kawamatsu et al., "Studies on Antihyperlipidemic Agents," Central Research Division, Takeda Chemical Industries, Ltd., Osaka (Japan) pp. 454–459.

*Primary Examiner*—Kamal A. Saeed
(74) *Attorney, Agent, or Firm*—Oblon, Spivak, McClelland, Maier & Neustadt, P.C.

(57) ABSTRACT

A halogenobenzylaminopropionic acid derivative represented by the following formula (1):

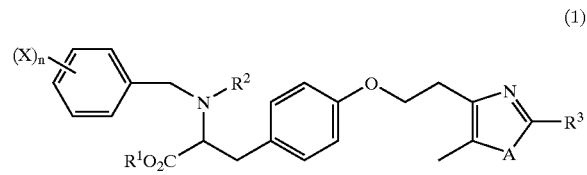

or a pharmaceutically acceptable salt of the derivative, and a drug containing the same as an active ingredient for treating diabetes, hyperlipidemia, or similar pathological conditions.

8 Claims, No Drawings

HALOGENOBENZYL AMINOPROPIONIC ACID DERIVATIVES

This application is a 371 of PCT/JP02/13573 filed Dec. 26, 2002.

TECHNICAL FIELD

The present invention relates to a halogenobenzylaminopropionic acid derivative which is useful as a preventive or therapeutic agent for diabetes and hyperlipidemia, and to a drug containing the derivative as an active ingredient.

BACKGROUND ART

In recent years, there have been a growing number of patients suffering from lifestyle-related diseases, especially such as diabetes and hyperlipidemia, as the eating habit of Japanese people is increasingly Westernized and they have less tendency to take exercise than did before. Diabetes and hyperlipidemia are known as critically basal diseases that could cause the development of arteriosclerosis and lead to ischemic heart diseases as a result.

Diabetes are classified into type I (insulin-dependent diabetes mellitus, IDDM) and type II (non-insulin-dependent diabetes mellitus, NIDDM). Sufferers of the latter type account for more than 90 percent of diabetic patients. In many cases, type II diabetes is complicated by hyperlipidemia. So that most patients with such a complicated type II diabetics often develop arteriosclerosis and subsequently ischemic heart diseases. Recent large-scale clinical studies have shown that the risks of these diseases are remarkably reduced by means of a therapy for lowering blood glucose, as well as by means of a therapy for lowering blood lipid (particularly, a therapy for effectively lowering blood triglyceride (hereinafter referred to as "blood TG")) (SENDCAP study (Diabetes Care (US), American Diabetes Association, 21, 641–648 (1998)); and DAIS study (Lancet (UK), Lancet, 357, 905–910 (2001))).

For example, the results of the DAIS study show that, when fenofibrate, which is known as a blood lipid lowering agent, is orally administered to diabetic patients complicated with hyperlipidemia in which a blood glucose level is sufficiently controlled, a decrease in average minimum lumen diameter and an increase in constriction degree, which indicate coronary artery lesion, are significantly suppressed, and a decrease in average lumen diameter, which indicates diffuse change, is significantly suppressed. The results also show a significant decrease in the number of deaths that were assumed to result from progress of coronary artery diseases, or a significant decrease in the occurrence of cardiovascular events. The above results show that sufficient control of blood glucose level and blood lipid is effective for treatment of patients with both type II diabetes and hyperlipidemia (the number of such patients has increased in recent years), and for prevention of arteriosclerosis and ischemic heart diseases resulting from arteriosclerosis, which are often developed by such patients. However, fenofibrate per se is well known to exhibit insufficient effect of lowering the blood glucose level of a diabetic patient. Therefore, demand has arisen for a drug exhibiting a high blood lipid lowering effect as well as a blood glucose lowering effect, which drug can be used as means for effectively treating patients with both type II diabetes and hyperlipidemia, and as means for preventing arteriosclerosis and ischemic heart diseases resulting from arteriosclerosis, which are developed by such patients.

Meanwhile, suppression of lowering of blood free fatty acid (hereinafter referred to as "blood FFA") has been reported to implicate insulin resistance (Khan, et al., Diabetologia (Germany), European Association for Study of Diabetes., 39 (Suppl), A53 (1996)).

Aminopropionic acid derivatives having a phenyloxazole structure have been reported as compounds exhibiting a blood lipid lowering effect as well as a blood glucose lowering effect (WO 96/38415, WO 97/31907, and WO 2000/08002).

Adiponectin, which is secreted from human adipose cells to the body, has been known to exhibit the effect of improving insulin resistance, which is a cause of type II diabetes.

DISCLOSURE OF THE INVENTION

As a result of extensive studies, we have found that a halogenobenzylaminopropionic acid derivative in which a hydrogen atom of the benzene ring of a benzyl group is substituted by a halogen atom exhibits remarkably potent blood glucose lowering effect and blood lipid lowering effect, as compared with a corresponding compound having no substituent on the benzene ring of the compound, and that the derivative is useful as a preventing or therapeutic agent for diabetes, hyperlipidemia, and similar diseases. The present invention has been accomplished on the basis of this finding.

Accordingly, the present invention provides a halogenobenzylaminopropionic acid derivative represented by the following formula (1):

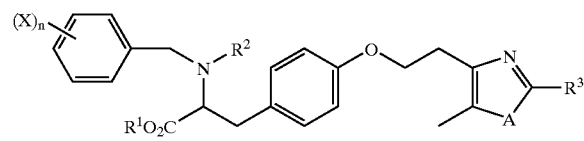

[wherein each of $R^1$ and $R^2$, which may be identical to or different from each other, represents a hydrogen atom or a lower alkyl group; $R^3$ represents a phenyl group which may have a substituent, a morpholinyl group, or a pyridinyl group; X represents a halogen atom; n represents an integer of 1 to 5; and A represents an oxygen atom or a sulfur atom]; or a pharmaceutically acceptable salt of the derivative.

The present invention also provides a halogenobenzylaminopropionic acid derivative represented by the aforementioned formula (1), or a pharmaceutically acceptable salt of the derivative.

The present invention also provides a drug composition comprising a halogenobenzylaminopropionic acid derivative represented by the aforementioned formula (1) or a pharmaceutically acceptable salt of the derivative, and a pharmaceutically acceptable carrier.

The present invention also provides use of a halogenobenzylaminopropionic acid derivative or a pharmaceutically acceptable salt of the derivative for producing a drug.

The present invention also provides a method for treating diabetes and/or hyperlipidemia, which comprises administering, to a subject in need thereof, an effective dose of a halogenobenzylaminopropionic acid derivative or a pharmaceutically acceptable salt of the derivative.

BEST MODE FOR CARRYING OUT THE INVENTION

Examples of the lower alkyl group represented by $R^1$ of formula (1) include C1–C4 linear or branched alkyl groups. Specific examples include a methyl group, an ethyl group, an n-propyl group, an n-butyl group, an isopropyl group, a tert-butyl group, and a sec-butyl group. Of these, a methyl group, an ethyl group, and an n-propyl group are preferred, with a methyl group and an ethyl group being more preferred.

Examples of the lower alkyl group represented by $R^2$ include C1–C4 linear or branched alkyl groups. Specific examples include a methyl group, an ethyl group, an n-propyl group, an n-butyl group, an isopropyl group, a tert-butyl group, and a sec-butyl group. Of these, a methyl group is preferred.

Examples of the phenyl group which may have a substituent represented by $R^3$ include a phenyl group, a phenyl group substituted by a halogen atom, and a phenyl group substituted by a lower alkyl group which may have a halogen atom. Examples of the halogen atom include a fluorine atom, a chlorine atom, a bromine atom, and an iodine atom. Examples of the lower alkyl group which may have a halogen atom include C1–C4 linear or branched alkyl groups in which one or more hydrogen atoms may be substituted by a halogen atom. Of these, a methyl group and a trifluoromethyl group are preferred. No particular limitations are imposed on the number of substituents on the phenyl group, and, when the number of the substituents is 2 or more, the substituents may differ from one another. No particular limitations are imposed on the positions of the substituents on the phenyl group. Examples of the phenyl group which may have a substituent include a phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,4,6-trifluorophenyl group, a pentafluorophenyl group, a 2-methylphenyl group, a 3-methylphenyl group, a 4-methylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2,4,6-trimethylphenyl group, a 2-trifluoromethylphenyl group, a 3-trifluoromethylphenyl group, and a 4-trifluoromethylphenyl group. Of these, a phenyl group, a 4-fluorophenyl group, a 4-methylphenyl group, and a 4-trifluoromethylphenyl group are preferred.

Examples of the morpholinyl group represented by $R^3$ include a 2-morpholinyl group, a 3-morpholinyl group, and a 4-morpholinyl group, with a 4-morpholinyl group being most preferred.

Examples of the pyridinyl group represented by $R^3$ include a 2-pyridinyl group, a 3-pyridinyl group, and a 4-pyridinyl group, with a 4-pyridinyl group being most preferred.

$R^3$ of formula (1) is preferably a phenyl group which may have a substituent.

Examples of the halogen atom represented by X include a fluorine atom, a chlorine atom, a bromine atom, and an iodine atom. Of these, a fluorine atom, a chlorine atom, or a bromine atom is preferred, with a fluorine atom and a chlorine atom being particularly preferred. In formula (1), n represents an integer of 1 to 5, and particularly, an integer of 1 to 3 is preferred. When n is 2 or more, the halogen atoms may differ from one another. No particular limitations are imposed on the position of X on the corresponding phenyl group. Depending on the number and position of X, the substituent on the phenyl group assumes various forms. Specific examples of the substituent include a 2-fluoro group, a 3-fluoro group, a 4-fluoro group, a 2-chloro group, a 3-chloro group, a 4-chloro group, a 2-bromo group, a 3-bromo group, a 4-bromo group, a 2-iodo group, a 3-iodo group, a 4-iodo group, a 2,3-difluoro group, a 2,4-difluoro group, a 2,5-difluoro group, a 2,6-difluoro group, a 3,4-difluoro group, a 3,5-difluoro group, a 2,4,6-trifluoro group, and a pentafluoro group. Of these, a 2-fluoro group, a 4-fluoro group, a 2-chloro group, a 4-chloro group, a 4-bromo group, a 2,3-difluoro group, a 2,4-difluoro group, a 2,6-difluoro group, a 3,4-difluoro group, a 2,4,6-trifluoro group, and a pentafluoro group are preferred.

Examples of the pharmaceutically acceptable salt of the compound represented by formula (1) of the present invention (hereinafter the compound may be referred to as "the present compound (1)") include alkali metal salts such as sodium salts and potassium salts; alkaline earth metal salts such as calcium salts and magnesium salts; inorganic acid salts such as hydrochlorides and sulfates; and organic acid salts such as oxalates, malonates, and methanesulfonates.

The present compound (1) has an asymmetric carbon atom, and thus has optical isomers attributed to the asymmetric carbon atom. The present invention encompasses these optical isomers and mixtures thereof. Particularly, optical isomers having an S configuration are preferred. The present compound (1) also encompasses hydrates and various solvates. The present compound (1) also encompasses all the crystal forms.

Specific examples of the present compound (1) include ethyl 3-[4-[2-(5-methyl-2-phenyl-1,3-oxazol-4-yl)ethoxy]phenyl]-2-(4-fluorobenzylamino)propionate, ethyl 3-[4-[2-[5-methyl-2-(4-methylphenyl)-1,3-oxazol-4-yl]ethoxy]phenyl]-2-(4-fluorobenzylamino)propionate, ethyl 3-[4-[2-(5-methyl-2-phenyl-1,3-thiazol-4-yl)ethoxy]phenyl]-2-(4-fluorobenzylamino)propionate, ethyl 3-[4-[2-[5-methyl-2-(morpholin-4-yl)-1,3-thiazol-4-yl]ethoxy]phenyl]-2-(4-fluorobenzylamino)propionate, methyl 3-[4-[2-(5-methyl-2-phenyl-1,3-oxazol-4-yl)ethoxy]phenyl]-2-(2,3-difluorobenzylamino)propionate, methyl 3-[4-[2-(5-methyl-2-phenyl-1,3-oxazol-4-yl)ethoxy]phenyl]-2-(2,6-difluorobenzylamino)propionate, methyl 3-[4-[2-(5-methyl-2-phenyl-1,3-oxazol-4-yl)ethoxy]phenyl]-2-(2,4,6-trifluorobenzylamino)propionate, methyl 3-[4-[2-(5-methyl-2-phenyl-1,3-oxazol-4-yl)ethoxy]phenyl]-2-(4-chlorobenzylamino)propionate, methyl 3-[4-[2-(5-methyl-2-phenyl-1,3-oxazol-4-yl)ethoxy]phenyl]-2-(2-chlorobenzylamino)propionate, 3-[4-[2-(5-methyl-2-phenyl-1,3-oxazol-4-yl)ethoxy]phenyl]-2-(4-fluorobenzylamino)propionic acid, 3-[4-[2-[2-(4-fluorophenyl)-5-methyl-1,3-oxazol-4-yl]ethoxy]phenyl]-2-(4-fluorobenzylamino)propionic acid, 3-[4-[2-[5-methyl-2-(4-methylphenyl)-1,3-oxazol-4-yl]ethoxy]phenyl]-2-(4-fluorobenzylamino)propionic acid, 3-[4-[2-[5-methyl-2-(4-trifluoromethylphenyl)-1,3-oxazol-4-yl]ethoxy]phenyl]-2-(4-fluorobenzylamino)propionic acid, 3-[4-[2-(5-methyl-2-phenyl-1,3-thiazol-4-yl)ethoxy]phenyl]-2-(4-fluorobenzylamino)propionic acid, 3-[4-[2-[5-methyl-2-(morpholin-4-yl)-1,3-thiazol-4-yl]ethoxy]phenyl]-2-(4-fluorobenzylamino)propionic acid, 3-[4-[2-(5-methyl-2-phenyl-1,3-oxazol-4-yl)ethoxy]phenyl]-2-(2-fluorobenzylamino)propionic acid, 3-[4-[2-(5-methyl-2-phenyl-1,3-oxazol-4-yl)ethoxy]phenyl]-2-(2,4-difluorobenzylamino)propionic acid, 3-[4-[2-(5-methyl-2-phenyl-1,3-oxazol-4-yl)ethoxy]phenyl]-2-(3,4-difluorobenzylamino)propionic acid, 3-[4-[2-(5-methyl-2- phenyl-1,3-oxazol-4-yl)ethoxy]phenyl]-2-(2,3-difluorobenzylamino)propionic acid, 3-[4-[2-(5-methyl-2-phenyl-1,3-oxazol-4-yl)ethoxy]phenyl]-2-(2,6-difluorobenzylamino)propionic acid, 3-[4-[2-(5-methyl-2-phenyl-1,3-oxazol-4-yl)ethoxy]phenyl]-2-(2,4,6-trifluorobenzylamino)propionic acid, 3-[4-[2-(5-methyl-2-phenyl-1,3-oxazol-4-yl)ethoxy]phenyl]-2-(pentafluorobenzylamino)propionic acid, 3-[4-[2-(5-methyl-2-phenyl-1,3-oxazol-4-yl)ethoxy]phenyl]-2-(4-chlorobenzylamino)propionic acid, 3-[4-[2-(5-methyl-2-phenyl-1,3-oxazol-4-yl)ethoxy]phenyl]-2-(2-chlorobenzylamino)propionic acid, 3-[4-[2-(5-methyl-2-phenyl-1,3-oxazol-4-yl)ethoxy]phenyl]-2-(4-bromobenzylamino)propionic acid, 3-[4-[2-(5-methyl-2-phenyl-1,3-oxazol-4-yl)ethoxy]phenyl]-2-[N-(4-fluorobenzyl)-N-methylamino]propionic acid, and pharmaceutically acceptable salts of these compounds. Optical isomers of these compounds having an S configuration are more preferred.

The present compound (1) can be produced through the process represented by the following reaction scheme:

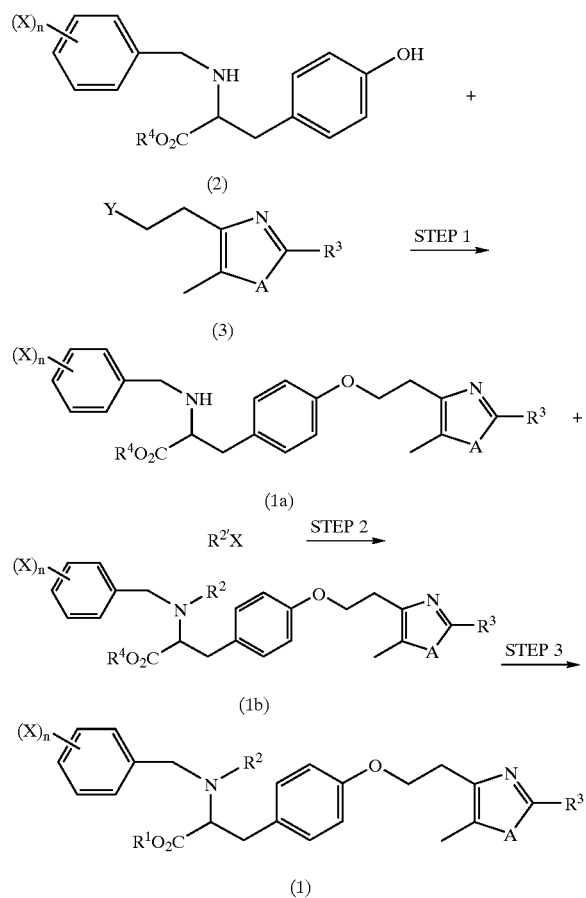

(wherein $R^1$, $R^2$, $R^3$, X, n, and A have the same meanings as described above, Y represents a substituent which can be subjected to condensation reaction (e.g., a hydroxyl group, a methanesulfonyloxy group, a p-toluenesulfonyloxy group, or a halogen atom), and each of $R^{2'}$ and $R^4$ represents a lower alkyl group (the definition of the lower alkyl group is the same as in the case of $R^1$)).

When R is a hydrogen atom, step 2 is not performed. When $R^1$ is a hydrogen atom, step 3 is performed. Steps 1 through 3 will next be described.

Step 1

In this step, the compound of formula (2) is condensed with the compound of formula (3), to thereby produce the compound of formula (1a). When Y of the compound of formula (3) is a hydroxyl group, the compound of formula (1a) can be produced by subjecting the compound of formula (2) and the compound of formula (3) to a reaction similar to a typical Mitsunobu reaction [e.g., O. Mitsunobu, Synthesis, 1 (1981), Tetsuto Tsunoda, et al., Journal of Synthetic Organic Chemistry, Japan, 55 (7), 631 (1997)]. Specifically, the compound of formula (1a) can be produced by reacting the compound of formula (2) and the compound of formula (3) with a Mitsunobu reagent (e.g., N,N,N',N'-tetramethylazodicarboxamide) at a reaction temperature of –10° C. to 80° C. for 1 to 48 hours in an aromatic hydrocarbon (e.g., benzene, toluene, or xylene), a halogenated hydrocarbon (e.g., dichloromethane or chloroform), an ether (e.g., diethyl ether, tetrahydrofuran, or dioxane), or a mixture of these solvents in the presence of a phosphine such as tributylphosphine.

When the compound of formula (3) has a group which is eliminated through nucleophilic reaction; i.e., when Y is, for example, a methanesulfonyloxy group, a p-toluenesulfonyloxy group, or a halogen atom, the compound of formula (1a) can be produced by subjecting the compound of formula (2) and the compound of formula (3) to a typical nucleophilic substitution reaction. Specifically, the compound of formula (1a) can be produced by reacting the compound of formula (2) and the compound of formula (3) with a base (e.g., metallic sodium, sodium hydride, sodium hydroxide, metallic potassium, potassium hydride, potassium carbonate, cesium carbonate, or rubidium carbonate) at a reaction temperature of –10° C. to the boiling point for 1 to 48 hours in an aromatic hydrocarbon (e.g., benzene, toluene, or xylene), a halogenated hydrocarbon (e.g., dichloromethane or chloroform), an ether (e.g., diethyl ether, tetrahydrofuran, or dioxane), an amide (e.g., dimethylacetamide or dimethylformamide), or a mixture of these solvents (if desired, in the presence of a reaction promoter such as sodium iodide, tetrabutylammonium halide, or tris [2-(2-methoxyethoxy)ethyl]amine).

Step 2

In this step, the compound of formula (1a) and an alkyl halide are subjected to a typical nucleophilic substitution reaction, to thereby produce the compound of formula (1b). Specifically, the compound of formula (1b) can be produced by reacting the compound of formula (1a) and an alkyl halide (e.g., methyl iodide or ethyl iodide) with a base (e.g., metallic sodium, sodium hydride, sodium hydroxide, metallic potassium, potassium hydride, or potassium carbonate) at a reaction temperature of –10° C. to the boiling point for 1 to 48 hours in an aromatic hydrocarbon (e.g., benzene, toluene, or xylene), a halogenated hydrocarbon (e.g., dichloromethane or chloroform), an ether (e.g., diethyl ether, tetrahydrofuran, or dioxane), an amide (e.g., dimethylacetamide or dimethylformamide), or a mixture of these solvents (if desired, in the presence of a reaction promoter such as sodium iodide or tetrabutylammonium halide).

Step 3

In this step, the lower alkyl group represented by $R^4$ is eliminated from the compound of formula (1b), to thereby produce the present compound (1). When $R^4$ of the compound of formula (1b) is a chain alkyl group such as a methyl group, an ethyl group, or an n-propyl group, the compound of formula (1) can be produced by subjecting the compound of formula (1b) to reaction at a reaction temperature of 0° C. to 100° C. for 1 to 48 hours in an alcohol (e.g., methanol or ethanol), an ether (e.g., diethyl ether, tetrahydrofuran, or dioxane), water, or a mixture of these solvents in the presence of a base such as an alkali metal hydroxide (e.g., sodium hydroxide or potassium hydroxide).

When $R^4$ of the compound of formula (1b) is, for example, a tert-butyl group, the compound of formula (1) or a pharmaceutically acceptable salt thereof can be produced by reacting the compound of formula (1b) with an organic acid such as formic acid, acetic acid, or trifluoroacetic acid or with an inorganic acid such as hydrochloric acid or sulfuric acid at a reaction temperature of 0° C. to 100° C. for 10 minutes to 12 hours in an alcohol (e.g., methanol or ethanol), an ether (e.g., diethyl ether, tetrahydrofuran, or dioxane), or a mixture of these solvents, or in the absence of a solvent.

The compound of formula (1) of the present invention can be formed into pharmaceutically acceptable salts (with acid or base) by means of a customary method. The salt form varies in accordance with the type of the compound. Examples of the salts include inorganic acid salts such as a hydrochloride, a hydrobromide, a hydroiodide, a sulfate, a nitrate, and a phosphate; organic acid salts such as an acetate, a trifluoroacetate, an oxalate, a fumarate, a maleate, a tartrate, a methanesulfonate, and a p-toluenesulfonate; alkali metal salts such as a sodium salt and a potassium salt; and alkaline earth metal salts such as a calcium salt.

The compound of formula (1a) can also be readily produced through the following process:

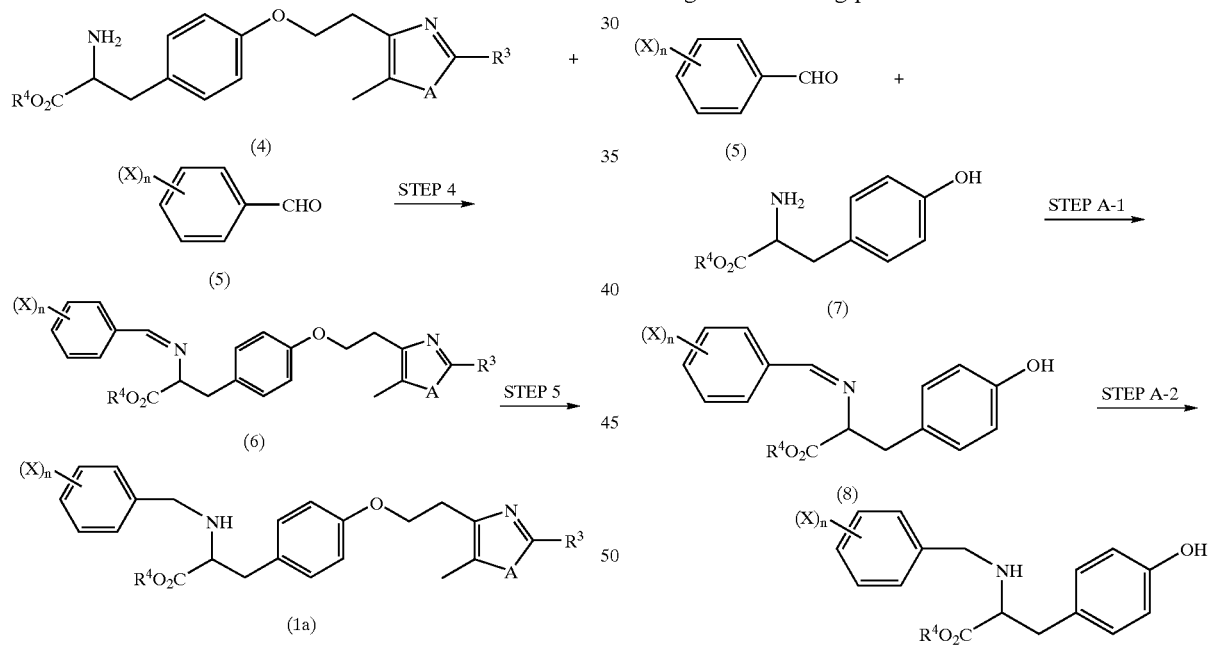

(wherein $R^3$, $R^4$, X, n, and A have the same meanings as described above).

Steps 4 and 5 will next be described.

Step 4

In this step, the compound of formula (4) is condensed with the compound of formula (5), to thereby produce the compound of formula (6). Reaction is performed by use of, if desired, an acid catalyst (e.g., acetic acid, p-toluenesulfonic acid, or sulfuric acid) and/or a dehydrating agent (e.g., molecular sieves or silica gel). Specifically, the compound of formula (6) can be produced by reacting the compound of formula (4) with the compound of formula (5) at a reaction temperature of 0° C. to 120° C. for one hour to one week in an alcohol (e.g., methanol or ethanol), an ether (e.g., diethyl ether, tetrahydrofuran, or dioxane), an aromatic hydrocarbon (e.g., benzene or toluene), or a mixture of these solvents (if desired, in the presence of an acid catalyst and/or a dehydrating agent).

When the compound of formula (4) is in the form of a salt such as a hydrochloride, preferably, the compound is neutralized with an organic base such as triethylamine or with an inorganic base such as sodium hydroxide, sodium hydrogencarbonate, sodium carbonate, potassium hydroxide, potassium hydrogencarbonate, or potassium carbonate, and the thus-neutralized compound is subjected to reaction.

Step 5

In this step, the imine moiety of the compound of formula (6) is reduced, to thereby produce the compound of formula (1a). Specifically, the compound of formula (1a) can be produced by subjecting the compound of formula (6) to reduction reaction employing a reducing agent (e.g., sodium borohydride, sodium triacetoxyborohydride, or sodium cyanoborohydride) or to catalytic reduction reaction (in the presence of palladium-carbon) at a reaction temperature of −10° C. to 80° C. for 1 to 48 hours in an alcohol (e.g., methanol or ethanol), an ether (e.g., diethyl ether, tetrahydrofuran, or dioxane), or a mixture of these solvents. The compound of formula (1a) can also be produced by means of a known imine reduction process.

The compound of formula (2) can be readily produced through the following process:

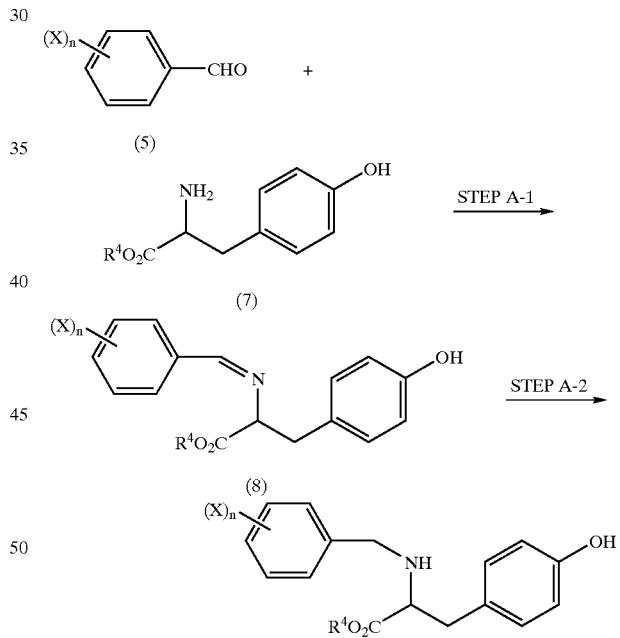

(wherein $R^4$, X, and n have the same meanings as described above).

Steps A-1 and A-2 will next be described.

Step A-1

In this step, the compound of formula (5) is condensed with the compound of formula (7), to thereby produce the compound of formula (8). Reaction is performed by use of, if desired, an acid catalyst (e.g., acetic acid, p-toluenesulfonic acid, or sulfuric acid) and/or a dehydrating agent (e.g., molecular sieves or silica gel). Specifically, the compound of formula (8) can be produced by reacting the compound of formula (5) with the compound of formula (7) at a reaction temperature of 0° C. to 120° C. for one hour to one week in an alcohol (e.g., methanol or ethanol), an ether (e.g., diethyl ether, tetrahydrofuran, or dioxane), an aromatic hydrocarbon (e.g., benzene or toluene), or a mixture of these solvents (if desired, in the presence of an acid catalyst and/or a dehydrating agent).

When the compound of formula (7) is in the form of a salt such as a hydrochloride, preferably, the compound is neutralized with an organic base such as triethylamine or with an inorganic base such as sodium hydroxide, sodium hydrogencarbonate, sodium carbonate, potassium hydroxide, potassium hydrogencarbonate, or potassium carbonate, and the thus-neutralized compound is subjected to reaction.

Step A-2

In this step, the imine moiety of the compound of formula (8) is reduced, to thereby produce the compound of formula (2). Specifically, the compound of formula (2) can be produced by subjecting the compound of formula (8) to reduction reaction employing a reducing agent (e.g., sodium borohydride, sodium triacetoxyborohydride, or sodium cyanoborohydride) or to catalytic reduction reaction (in the presence of palladium-carbon) at a reaction temperature of −10° C. to 80° C. for 1 to 48 hours in an alcohol (e.g., methanol or ethanol), an ether (e.g., diethyl ether, tetrahydrofuran, or dioxane), or a mixture of these solvents. The compound of formula (2) can also be produced by means of a known imine reduction process.

The compound of formula (4) can be readily produced through the following process:

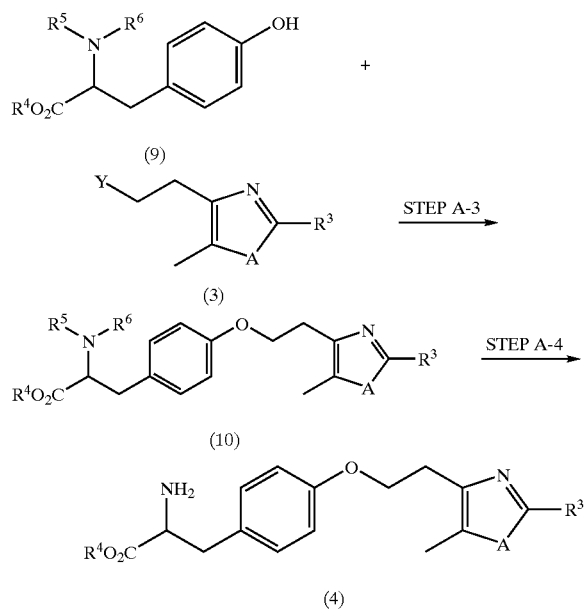

(wherein $R^3$, $R^4$, A, and Y have the same meanings as described above, $R^5$ represents an amino protective group, and $R^6$ represents a hydrogen atom or an amino protective group, with the proviso that $R^5$ and $R^6$ may together form an amino protective group).

The amino protective group (represented by $R^5$ or $R^6$) is a generally known protective group. Examples of the protective group include an aralkyl group (e.g., a benzyl group, a diphenylmethyl group, or a trityl group), a tert-butoxycarbonyl group, and a benzyloxycarbonyl group. When $R^5$ and $R^6$ together form an amino protective group, the protective group is, for example, a phthaloyl group.

Steps A-3 and A-4 will next be described.

Step A-3

In this step, the compound of formula (9) is condensed with the compound of formula (3), to thereby produce the compound of formula (10). When Y of the compound of formula (3) is a hydroxyl group, the compound of formula (10) can be produced by subjecting the compound of formula (9) and the compound of formula (3) to a reaction similar to a typical Mitsunobu reaction. Specifically, the compound of formula (10) can be produced by reacting the compound of formula (9) and the compound of formula (3) with a Mitsunobu reagent (e.g., diisopropyl azodicarboxylate) at a reaction temperature of −10° C. to 80° C. for 1 to 48 hours in an aromatic hydrocarbon (e.g., benzene, toluene, or xylene), a halogenated hydrocarbon (e.g., dichloromethane or chloroform), an ether (e.g., diethyl ether, tetrahydrofuran, or dioxane), or a mixture of these solvents in the presence of a phosphine such as triphenylphosphine.

When the compound of formula (3) has a group which is eliminated through nucleophilic reaction; i.e., when Y is, for example, a methanesulfonyloxy group, a p-toluenesulfonyloxy group, or a halogen atom, the compound of formula (10) can be produced by subjecting the compound of formula (9) and the compound of formula (3) to a typical nucleophilic substitution reaction. Specifically, the compound of formula (10) can be produced by reacting the compound of formula (9) and the compound of formula (3) with a base (e.g., metallic sodium, sodium hydride, sodium hydroxide, metallic potassium, potassium hydride, potassium carbonate, cesium carbonate, or rubidium carbonate) at a reaction temperature of −10° C. to the boiling point for 1 to 48 hours in an aromatic hydrocarbon (e.g., benzene, toluene, or xylene), a halogenated hydrocarbon (e.g., dichloromethane or chloroform), an ether (e.g., diethyl ether, tetrahydrofuran, or dioxane), an amide (e.g., dimethylacetamide or dimethylformamide), or a mixture of these solvents (if desired, in the presence of a reaction promoter such as sodium iodide, tetrabutylammonium halide, or tris [2-(2-methoxyethoxy)ethyl]amine).

Step A-4

In this step, the amino protective group (represented by $R^5$ and/or $R^6$) is eliminated from the compound of formula (10), to thereby produce the compound of formula (4). When $R^5$ and/or $R^6$ of the compound of formula (10) are, for example, a tert-butoxycarbonyl group, the compound of formula (4) can be produced by reacting the compound of formula (10) with an organic acid such as formic acid, acetic acid, or trifluoroacetic acid or with an inorganic acid such as hydrochloric acid or sulfuric acid at a reaction temperature of 0° C. to 100° C. for 10 minutes to 12 hours in an alcohol (e.g., methanol or ethanol), an ether (e.g., diethyl ether, tetrahydrofuran, or dioxane), or a mixture of these solvents, or in the absence of a solvent.

Meanwhile, when $R^5$ and/or $R^6$ of the compound of formula (10) are, for example, an aralkyl group or a benzyloxycarbonyl group, the compound of formula (4) is produced by subjecting the compound of formula (10) to catalytic hydrogenation. Specifically, the compound of formula (4) can be produced by subjecting the compound of formula (10) to catalytic reduction reaction (in the presence of palladium-carbon) at a reaction temperature of −10° C. to 80° C. for 1 to 48 hours in an alcohol (e.g., methanol or ethanol), an ether (e.g., diethyl ether, tetrahydrofuran, or dioxane), or a mixture of these solvents.

When $R^5$ and $R^6$ of the compound of formula (10) together form an amino protective group (e.g., a phthaloyl group), the compound of formula (4) can be produced by subjecting the compound of formula (10) to reaction at a reaction temperature of 0° C. to 100° C. for 1 to 48 hours in an alcohol (e.g., methanol or ethanol), an ether (e.g., diethyl ether, tetrahydrofuran, or dioxane), a halogenated hydrocarbon (e.g., dichloromethane or chloroform), or a mixture of these solvents in the presence of a hydrazine compound (e.g., hydrazine) or a primary amine (e.g., methylamine or ethylamine).

The thus-produced present compound (1) or a pharmaceutically acceptable salt thereof exhibits excellent blood glucose lowering effect and blood lipid (TG and FFA) lowering effect, as shown in the below-described Test Examples. For example, the present compound (1) or a pharmaceutically acceptable salt thereof is useful as drugs for animals (including human), including a preventive or therapeutic agent for diabetes (e.g., insulin-dependent diabetes mellitus, non-insulin-dependent diabetes mellitus, or gestational diabetes mellitus), a preventive or therapeutic agent for hyperlipidemia (e.g., hypertriglyceridemia, hypercholesterolemia, or hypoHDLemia), an insulin sensitivity enhancing agent, an insulin resistance improving agent, a preventive or therapeutic agent for impaired glucose tolerance (IGT), and an agent for preventing progression from impaired glucose tolerance to diabetes. The present compound (1) or a pharmaceutically acceptable salt thereof is also useful as a preventing or therapeutic agent for, for example, diabetic complications (e.g., neurosis, nephropathy, retinopathy, cataract, macroangiopathy, and osteopenia), obesity, osteoporosis, cachexia (e.g., cancerous cachexia or diabetic cachexia), fatty liver, hypertension, kidney diseases (e.g., diabetic nephropathy and glomerulonephritis), myocardial infarction, angina pectoris, cerebral infarction, insulin resistant syndrome, syndrome X, perception disorder by hyperinsulinemia, tumor (e.g., prostatic cancer), inflammatory diseases (e.g., chronic articular rheumatism and spondylosis deformans), and arteriosclerosis (e.g., atherosclerosis).

The present compound (1) or a pharmaceutically acceptable salt thereof may be incorporated into a pharmaceutically acceptable carrier, and the resultant drug composition may be administered orally or parenterally (e.g., through intravenous or intramuscular injection).

Examples of oral formulations include tablets (including sugar-coated tablets and film-coated tablets), pills, granules, powders, capsules (including soft capsules), syrups, emulsions, and suspensions. These oral formulations can be produced by combining the present compound (1) or a pharmaceutically acceptable salt thereof with one or more additives which are generally employed in the manufacture of drugs, through a known method. Examples of the additives which may be employed include excipients such as lactose, mannitol, and anhydrous calcium hydrogenphosphate; binders such as hydroxypropyl cellulose, methyl cellulose, and polyvinyl pyrrolidone; disintegrating agents such as starch and carboxymethyl cellulose; and lubricants such as magnesium stearate and talc.

Examples of parenteral formulations include injections. Injection products are produced through a known method; for example, injections are produced by dissolving the present compound (1) or a pharmaceutically acceptable salt thereof into water for injection as specified by Japanese Pharmacopoeia. If desired, injections may contain, for example, isotonizing agents such as sodium chloride and buffer agents such as sodium hydrogenphosphate or sodium monohydrogenphosphate.

The daily dose of the present compound (1) for an adult patient differs depending on, for example, the medical condition, body weight, and age of the patient, the type of the compound, and the administration route. In the case of oral administration, the daily dose is appropriately about 0.01 to 1,000 mg, preferably about 0.01 to 100 mg. In the case of parenteral administration, the daily dose is preferably ⅒ to ½ that in the case of oral administration. The daily dose of the compound may be appropriately increased or decreased in consideration of, for example, the medical condition, body weight, and age of the patient.

EXAMPLES

The present invention will next be described in more detail with reference to referential examples, examples, a comparative example, and a test example. However, the present invention should not be construed as being limited to these examples.

Referential Example 1

(S)—N-(4-Fluorobenzyl)tyrosine Ethyl Ester (Referential Compound 1)

An (S)-tyrosine hydrochloride ethyl ester (61.5 g) and triethylamine (42 mL) were dissolved in methanol (250 mL), and molecular sieve 4A was added thereto. 4-Fluorobenzaldehyde (30 mL) was added dropwise thereto at 0° C., and the mixture was stirred for five hours at room temperature. Formation of an imine was confirmed through thin-layer chromatography. After the reaction mixture was cooled in an ice bath, sodium borohydride (10.4 g) was added thereto, and the mixture was stirred overnight at room temperature. The reaction mixture was filtered by use of celite, and the solvent was distilled off at low temperature. Water was added to the residue, and the mixture was subjected to extraction with chloroform. The organic layer was concentrated and then diluted with diethyl ether. A diethyl ether solution saturated with hydrogen chloride was added thereto, and the mixture was subjected to extraction with water. A 10-%(w/v) aqueous sodium hydroxide solution was added dropwise to the aqueous layer, to thereby adjust the pH of the mixture to 12. The resultant mixture was subjected to extraction with diethyl ether and ethyl acetate, and the solvent was distilled off, to thereby yield 67.3 g of the title compound as a colorless oil.

IRν max (neat): 3382, 2977, 2930, 2846, 1731, 1614, 1515, 1460, 1377, 1223, 1107, 1023, 825 cm$^{-1}$.

$^1$H-NMR(CDCl$_3$)δ: 1.25(3H, t, J=7.0 Hz), 2.97(2H, d, J=6.8 Hz), 3.53(1H, t, J=6.8 Hz), 3.69(1H, d, J=13.0 Hz), 3.84(1H, d, J=13.0 Hz), 4.17(2H, q, J=7.0 Hz), 6.74(2H, d, J=8.6 Hz), 6.93–7.04(4H, m), 7.23–7.28(2H, m).

Referential Example 2

(S)-3-[4-[2-(5-Methyl-2-phenyl-1,3-oxazol-4-yl) ethoxy]phenyl]-2-[N-tert-butoxycarbonyl-(4-fluorobenzyl)amino]propionic Acid (Referential Compound 2)

Under argon atmosphere, Compound 18 (200 mg) was added to 1,4-dioxane (4 mL) and water (2 mL), to thereby yield a dispersion solution. Triethylamine (520 μL) and di-tert-butyldicarbonate (214 μL) were added thereto at 0° C., and the mixture was stirred for one hour at room temperature. The solvent was removed under reduced pressure, and the residue was diluted with chloroform. The organic layer was washed with a 10-%(w/v) aqueous citric acid solution, water, and saturated brine and dried over anhydrous sodium sulfate. Subsequently, the solvent was removed under reduced pressure, and the thus-obtained crude product was subjected to purification through silica gel column chromatography (chloroform:methanol=30:1 to 10:1), to thereby yield 199.7 mg of the title compound as a colorless amorphous compound.

IRν max(neat): 3060, 2977, 2929, 2874, 2558, 1698, 1654, 1609, 1558, 1510, 1458, 1247, 1223, 1155, 1025, 826, 757, 692 cm$^{-1}$.

$^1$H-NMR(CDCl$_3$)δ: 1.26(9H, s), 2.40(3H, s), 3.00(2H, t, J=6.7 Hz), 3.13–3.28(2H, m), 3.49–3.77(2H, m), 4.01(1H, brs), 4.23(2H, t, J=6.7 Hz), 6.79(2H, d, J=8.3 Hz), 6.85–6.98 (6H, m), 7.41–7.43(3H, m), 8.00(2H, brs).

Referential Example 3

Methyl (S)-3-[4-[2-(5-methyl-2-phenyl-1,3-oxazol-4-yl)ethoxy]phenyl]-2-aminopropionate hydrochloride (Referential Compound 3)

Under argon atmosphere, an L-tert-butoxycarbonyltyrosine methyl ester (15.3 g) and 2-(5-methyl-2-phenyl-1,3-oxazol-4-yl)ethanol (11.6 g) were dissolved in toluene (500 mL), and triphenylphosphine (16.3 g) was added to the resultant mixture. Diisopropyl azodicarboxylate (11.2 mL) was added dropwise thereto under cooling with ice. After completion of addition, the mixture was stirred overnight at room temperature. Water (500 mL) was added to the reaction mixture, and the mixture was subjected to extraction with ethyl acetate. The organic layer was washed with a 1-mol/L aqueous sodium hydroxide solution, water, and saturated brine, and dried over anhydrous sodium sulfate. Subsequently, the solvent was removed under reduced pressure, to thereby yield a pale yellow syrup. The product was dissolved in dioxane (160 mL), and a 1,4-dioxane solution saturated with hydrogen chloride (80 mL) was added dropwise to the solution, followed by stirring overnight. The solvent was removed under reduced pressure, and acetone (500 mL) was added to the residue. The precipitate was collected through filtration, washed with acetone and diisopropyl ether, and dried, to thereby yield 19.2 g of the title compound as a colorless powder.

IRν max(KBr): 3448, 3030, 2856, 2632, 1846, 1732, 1676, 1610, 1577, 1512, 1444, 1289, 1245, 1181, 1025 cm$^{-1}$.

$^1$H-NMR(CD$_3$OD)δ: 2.41(3H, s), 2.98–3.22(4H, m), 3.79 (3H, s), 4.22–4.27(3H, m), 6.93(2H, d, J=8.6 Hz), 7.14(2H, d, J=8.6 Hz), 7.48–7.50(3H, m), 7.95–7.98(2H, m).

Example 1

Ethyl(S)-3-[4-[2-(5-methyl-2-phenyl-1,3-oxazol-4-yl)ethoxy]phenyl]-2-(4-fluorobenzylamino) propionate (Compound 1)

To a solution of Referential Compound 1 (6.22 g) in toluene (200 mL), 2-(5-methyl-2-phenyl-1,3-oxazol-4-yl) ethanol (5.97 g) and tributylphosphine (9.8 mL) were added, and the mixture was stirred for 30 minutes at room temperature. While the reactor was cooled in an ice bath, 1,1'-azobis(N,N-dimethylformamide) (6.75 g) was added thereto portion wise, and the mixture was stirred overnight. Water (200 mL) was added to the reaction mixture, and the resultant mixture was subjected to extraction with ethyl acetate. The organic layer was washed with saturated brine and dried over anhydrous magnesium sulfate. Subsequently, the solvent was removed under reduced pressure, and the thus-obtained crude product was subjected to purification through silica gel column chromatography (ethyl acetate:hexane=1:3 to 1:2), to thereby yield 7.73 g of the title compound as a pale yellow oil.

IRν max(neat): 3330, 3060, 3033, 2977, 2929, 1731, 1643, 1611, 1555, 1511, 1471, 1373, 1293, 1247, 1219, 1179, 1025 cm$^{-1}$.

$^1$H-NMR(CDCl$_3$)δ: 1.18(3H, t, J=7.1 Hz), 2.37(3H, s), 2.95(2H, d, J=6.6 Hz), 3.04(2H, t, J=6.8 Hz), 3.55(1H, t, J=6.6 Hz), 3.75(1H, d, J=13.8 Hz), 3.85(1H, d, J=13.8 Hz), 4.12(2H, q, J=7.1 Hz), 4.21(2H, t, J=6.8 Hz), 6.80(2H, d, J=8.6 Hz), 6.94–7.06(5H, m), 7.30(1H, dd, J=8.5, 5.7 Hz), 7.39–7.44(3H, m), 7.97(2H, d, J=8.1 Hz).

m/z(ESI+): 503(M+H)$^+$.

$[α]_D^{29}$ (CHCl$_3$): +1.7(c=1.6).

Example 2

Ethyl(S)-3-[4-[2-[2-(4-fluorophenyl)-5-methyl-1,3-oxazol-4-yl]ethoxy]phenyl]-2-(4-fluorobenzylamino) propionate (Compound 2)

In the same manner as in Example 1, 232.6 mg of the title compound was obtained as colorless oil from 187.1 mg of Referential Compound 1 and 195.6 mg of 2-[2-(4-fluorophenyl)-5-methyl-1,3-oxazol-4-yl]ethanol.

IRν max(neat): 3335, 3036, 2980, 2928, 2874, 1731, 1644, 1608, 1559, 1507, 1471, 1416, 1373, 1298, 1222, 1179, 1156, 1024, 949, 842, 737, 620 cm$^{-1}$.

$^1$H-NMR(CDCl$_3$)δ: 1.20(3H, t, J=7.2 Hz), 2.36(3H, s), 2.92–3.02(4H, m), 3.47–3.55(1H, m), 3.65–3.74(1H, m), 3.76–3.84(1H, m), 4.12(2H, q, J=7.2 Hz), 4.20(2H, t, J=6.8 Hz), 6.80(2H, d, J=8.4 Hz), 6.92–7.01(2H, m), 7.07(2H, d, J=8.4 Hz), 7.10(2H, t, J=8.6 Hz), 7.20–7.29(2H, m), 7.92–8.00(2H, m).

Example 3

Ethyl(S)-3-[4-[2-[5-methyl-2-(4-methylphenyl)-1,3-oxazol-4-yl]ethoxy]phenyl]-2-(4-fluorobenzylamino) propionate (Compound 3)

In the same manner as in Example 1, 219.5 mg of the title compound was obtained as colorless oil from 200.0 mg of Referential Compound 1 and 205.3 mg of 2-[5-methyl-2-(4-methylphenyl)-1,3-oxazol-4-yl]ethanol.

IRν max(neat): 3336, 3032, 2924, 1730, 1643, 1612, 1583, 1557, 1511, 1470, 1372, 1296, 1245, 1220, 1177, 1020, 948, 824, 761, 731, 621 cm$^{-1}$.

$^1$H-NMR(CDCl$_3$)δ: 1.19(3H, t, J=7.2 Hz), 2.35(3H, s), 2.38(3H, s), 2.92-3.02(4H, m), 3.51(1H, t, J=6.4 Hz), 3.70 (1H, d, J=12.8 Hz), 3.80(0.1H, d, J=12.8 Hz), 4.12(2H, q, J=7.2 Hz), 4.20(2H, t, J=6.8 Hz), 6.80(2H, d, J=8.4 Hz), 6.96(2H, dd, J=8.6, 8.6 Hz), 7.06(2H, d, J=8.4 Hz), 7.20–7.28(4H, m), 7.85(2H, d, J=8.3 Hz).

Example 4

Ethyl(S)-3-[4-[2-[5-methyl-2-(4-trifluoromethylphenyl)-1,3-oxazol-4-yl]ethoxy] phenyl]-2-(4-fluorobenzylamino)propionate (Compound 4)

In the same manner as in Example 1, 226.4 mg of the title compound was obtained as colorless oil from 200.0 mg of Referential Compound 1 and 256.3 mg of 2-[5-methyl-2-(4-trifluoromethylphenyl)-1,3-oxazol-4-yl]ethanol.

IRν max(neat): 2976, 2930, 1731, 1617, 1509, 1473, 1416, 1323, 1245, 1221, 1167, 1127, 1083, 1063, 1016, 849, 714, 670 cm$^{-1}$.

¹H-NMR(CDCl₃)δ: 1.19(3H, t, J=7.2 Hz), 2.39(3H, s), 2.93–3.02(4H, m), 3.46–3.52(1H, m), 3.66(1H, d, J=13.0 Hz), 3.79(1H, d, J=13.0 Hz), 4.12(2H, q, J=7.2 Hz), 4.21 (2H, t, J=6.6 Hz), 6.80(2H, d, J=8.6 Hz), 6.95(2H, dd, J=8.6, 8.6 Hz), 7.07(2H, d, J=8.6 Hz), 7.19–7.25(2H, m), 7.67(2H, d, J=8.1 Hz), 8.08(2H, d, J=8.1 Hz).

Example 5

Ethyl(S)-3-[4-[2-(5-methyl-2-phenyl-1,3-thiazol-4-yl)ethoxy]phenyl]-2-(4-fluorobenzylamino)propionate (Compound 5)

In the same manner as in Example 1, 172.0 mg of the title compound was obtained as colorless oil from 186.0 mg of Referential Compound 1 and 192.8 mg of 2-(5-methyl-2-phenyl-1,3-thiazol-4-yl)ethanol.

IRν max(neat): 3339, 3060, 2976, 2927, 2874, 1730, 1610, 1545, 1509, 1462, 1373, 1298, 1243, 1178, 1130, 1029, 970, 824, 762, 690 cm⁻¹.

¹H-NMR(CDCl₃)δ: 1.19(3H, t, J=7.2 Hz), 2.45(3H, s), 2.94–3.01(2H, m), 3.18(2H, t, J=7.0 Hz), 3.46–3.55(1H, m), 3.68(1H, d, J=13.4 Hz), 3.80(1H, d, J=13.4 Hz), 4.12(2H, q, J=7.2 Hz), 4.29(2H, t, J=7.0 Hz), 6.81(2H, d, J=8.4 Hz), 6.96(2H, dd, J=8.6, 8.6 Hz), 7.06(2H, d, J=8.4 Hz), 7.21–7.30(2H, m), 7.35–7.44(3H, m), 7.83–7.88(2H, m).

Example 6

Ethyl(S)-3-[4-[2-[5-methyl-2-(morpholin-4-yl)-1,3-thiazol-4-yl]ethoxy]phenyl]-2-(4-fluorobenzylamino)propionate (Compound 6)

In the same manner as in Example 1, 148.8 mg of the title compound was obtained as colorless oil from 200.0 mg of Referential Compound 1 and 215.8 mg of 2-[5-methyl-2-(morpholin-4-yl)-1,3-thiazol-4-yl]ethanol.

IRν max(neat): 3330, 2963, 2921, 2857, 1731, 1610, 1512, 1455, 1374, 1300, 1268, 1231, 1179, 1118, 1026, 941, 876, 825, 674, 638 cm⁻¹.

¹H-NMR(CDCl₃)δ: 1.20(3H, t, J=7.2 Hz), 2.26(3H, s), 2.89–3.00(4H, m), 3.35–3.50(5H, m), 3.62(1H, d, J=13.0 Hz), 3.74–3.83(5H, m), 4.12(2H, q, J=7.2 Hz), 4.18(2H, t, J=6.8 Hz), 6.79(2H, d, J=8.4 Hz), 6.95(2H, dd, J=7.3, 7.3 Hz), 7.05(2H, d, J=8.4 Hz), 7.20(2H, dd, J=7.3, 5.0 Hz).

Example 7

Methyl(S)-3-[4-[2-(5-methyl-2-phenyl-1,3-oxazol-4-yl)ethoxy]phenyl]-2-(2-fluorobenzylamino)propionate (Compound 7)

Referential Compound 3 (208.5 mg) was dissolved in water (15 mL), and a 0.5-mol/L aqueous ammonium hydrogencarbonate solution was added thereto under cooling with ice, to thereby adjust the pH of the mixture to 8. The formed aqueous layer was subjected to extraction with ethyl acetate, and the organic layer was dried over anhydrous sodium sulfate. The solvent was removed under reduced pressure, to thereby yield methyl(S)-3-[4-[2-(5-methyl-2-phenyl-1,3-oxazol-4-yl)ethoxy]phenyl]-2-aminopropionate as a colorless oil. The product was dissolved in methanol (10 mL), and, while the solution was cooled with ice, 2-fluorobenzaldehyde (79.0 μL) and sodium triacetoxyborohydride (160.1 mg) were added thereto, followed by stirring for 1.5 hours at 0° C. Sodium triacetoxyborohydride (79.9 mg) was further added thereto, and the mixture was stirred for 1.5 hours at 0° C. Acetone (1 mL) was added thereto, and the solvent was removed under reduced pressure. The thus-obtained crude product was subjected to purification through silica gel column chromatography (ethyl acetate:hexane=1:6 to 1:5), to thereby yield 98.8 mg of the title compound as a colorless solid.

IRν max(KBr): 3330, 3042, 2958, 2922, 2864, 1723, 1638, 1610, 1585, 1552, 1460, 1270, 1245, 1182, 1138, 1056, 1026, 759 cm⁻¹

¹H-NMR(CDCl₃)δ: 2.37(3H, s), 2.97(2H, t, J=6.8 Hz), 2.99(2H, brm), 3.57(1H, t, J=6.6 Hz), 3.63(3H, s), 3.83(1H, d, J=13.7 Hz), 3.91(1H, d, J=13.7 Hz), 4.22(2H, t, J=6.8 Hz), 6.81(2H, d, J=6.6 Hz), 6.96–7.10(4H, m), 7.20–7.46(5H, m), 7.96–7.99(2H, m).

Example 8

Methyl(S)-3-[4-[2-(5-methyl-2-phenyl-1,3-oxazol-4-yl)ethoxy]phenyl]-2-(2,4-difluorobenzylamino)propionate (Compound 8)

In the same manner as in Example 7, 243.9 mg of the title compound was obtained as colorless amorphous compound from 421.3 mg of Referential Compound 3 and 240 μL of 2,4-difluorobenzaldehyde.

IRν max(neat): 3338, 3064, 3034, 2951, 2925, 2874, 1736, 1639, 1613, 1556, 1512, 1448, 1431, 1337, 1246, 1175, 1138, 1097, 1022, 962, 849, 715, 693 cm⁻¹.

¹H-NMR(CDCl₃)δ: 2.37(3H, s), 2.97(2H, t, J=6.5 Hz), 2.95–2.99(2H, m), 3.53(1H, t, J=7.5 Hz), 3.65(3H, s), 3.76 (1H, d, J=13.4 Hz), 3.85(1H, d, J=13.4 Hz), 4.22(2H, t, J=6.5 Hz), 6.71–6.78(2H, m), 6.81(2H, d, J=8.4 Hz), 7.06(2H, d, J=8.4 Hz), 7.26–7.33(1H, m), 7.40–7.43(3H, m), 7.96–7.99 (2H, m).

Example 9

Methyl(S)-3-[4-[2-(5-methyl-2-phenyl-1,3-oxazol-4-yl)ethoxy]phenyl]-2-(3,4-difluorobenzylamino)propionate (Compound 9)

In the same manner as in Example 7, 213.3 mg of the title compound was obtained as colorless amorphous compound from 490.8 mg of Referential Compound 3 and 215 μL of 3,4-difluorobenzaldehyde.

IRν max(neat): 3345, 3061, 3036, 2994, 2951, 2925, 2875, 1734, 1637, 1611, 1556, 1514, 1434, 1283, 1246, 1203, 1175, 1114, 1021, 949, 821, 776, 715, 693 cm⁻¹.

¹H-NMR(CDCl₃)δ: 2.37(3H, s), 2.97(2H, t, J=6.6 Hz), 2.95–3.12(2H, m), 3.54(1H, brs), 3.69(3H, s), 3.69–3.79 (1H, m), 3.81(1H, d, J=12.3 Hz), 4.22(2H, t, J=6.6 Hz), 6.82(2H, d, J=8.3 Hz), 7.06(2H, d, J=8.3 Hz), 6.95–7.18(3H, m), 7.40–7.43(3H, m), 7.96–7.99(2H, m).

Example 10

Methyl(S)-3-[4-[2-(5-methyl-2-phenyl-1,3-oxazol-4-yl)ethoxy]phenyl]-2-(2,3-difluorobenzylamino)propionate (Compound 10)

In the same manner as in Example 7, 253.2 mg of the title compound was obtained as colorless oil from 510.0 mg of Referential Compound 3 and 191 μL of 2,3-difluorobenzaldehyde.

IRν max(neat): 3337, 3034, 2951, 2925, 2874, 1733, 1636, 1612, 1556, 1513, 1488, 1448, 1338, 1284, 1246, 1175, 1142, 1022, 949, 825, 776, 716, 693 cm⁻¹.

¹H-NMR(CDCl₃)δ: 2.37(3H, s), 2.97(2H, t, J=6.6 Hz), 2.88–2.99(2H, m), 3.51(1H, t, J=6.7 Hz), 3.65(3H, s), 3.79

(1H, d, J=13.7 Hz), 3.89(1H, d, J=13.7 Hz), 4.22(2H, t, J=6.6 Hz), 6.81(2H, d, J=8.5 Hz), 6.97–7.07(3H, m), 7.05(2H, d, J=8.5 Hz), 7.39–7.46(3H, m), 7.96–7.99(2H, m).

Example 11

Methyl(S)-3-[4-[2-(5-methyl-2-phenyl-1,3-oxazol-4-yl)ethoxy]phenyl]-2-(2,6-difluorobenzylamino)propionate (Compound 11)

In the same manner as in Example 7, 570.3 mg of the title compound was obtained as colorless powder from 600.8 mg of Referential Compound 3 and 220 µL of 2,6-difluorobenzaldehyde.

IRν max(KBr): 3351, 3069, 2955, 2923, 2899, 2873, 1725, 1640, 1626, 1590, 1552, 1514, 1469, 1438, 1387, 1337, 1303, 1267, 1234, 1202, 1183, 1136, 1071, 1055, 1027, 981, 896, 817, 803, 787, 774, 709, 691, 670, 622 cm$^{-1}$.

$^1$H-NMR(CDCl$_3$)δ: 2.36(3H, s), 2.90-3.00(4H, m), 3.51 (1H, t, J=6.9 Hz), 3.57(3H, s), 3.88(2H, s), 4.21(2H, t, J=6.6 Hz), 6.78(2H, d, J=8.4 Hz), 6.84(2H, d, J=7.8 Hz), 7.02(2H, d, J=8.4 Hz), 7.14–7.22(1H, m), 7.38–7.46(3H, m), 7.95–8.00(2H, m).

Example 12

Methyl(S)-3-[4-[2-(5-methyl-2-phenyl-1,3-oxazol-4-yl)ethoxy]phenyl]-2-(2,4,6-trifluorobenzylamino)propionate (Compound 12)

In the same manner as in Example 7, 351.5 mg of the title compound was obtained as pale yellow amorphous compound from 421.3 mg Referential compound 3 and 274 mg of 2,4,6-trifluorobenzaldehyde.

IRν max(KBr): 3066, 2952, 2874, 1734, 1717, 1645, 1625, 1608, 1557, 1512, 1338, 1246, 1173, 1118, 1062, 1027, 998, 841, 776, 717, 693, 617 cm$^{-1}$.

$^1$H-NMR(CDCl$_3$)δ: 2.37(3H, s), 2.97(2H, t, J=6.6 Hz), 2.95–2.99(1H, m), 3.54(1H, brs), 3.61(3H, s), 3.85(2H, brs), 4.21(2H, t, J=6.6 Hz), 4.73(1H, brs), 6.61(1H, t, J=8.0 Hz), 6.68(1H, t, J=8.0 Hz), 6.80(2H, d, J=8.4 Hz), 7.04(2H, d, J=8.4 Hz), 7.41–7.43(3H, m), 7.97–7.99 (2H, m).

Example 13

Methyl(S)-3-[4-[2-(5-methyl-2-phenyl-1,3-oxazol-4-yl)ethoxy]phenyl]-2-(pentafluorobenzylamino)propionate (Compound 13)

In the same manner as in Example 7, 433.0 mg of the title compound was obtained as colorless oil from 591.2 mg of Referential Compound 3 and 250 µL of pentafluorobenzaldehyde.

IRν max(neat): 3348, 2952, 1732, 1652, 1614, 1557, 1507, 1472, 1455, 1338, 1299, 1245, 1129, 1021, 946, 831, 776, 716, 694 cm$^{-1}$.

$^1$H-NMR(CDCl$_3$)δ: 2.38(3H, s), 2.84–3.04(2H, m), 2.99 (2H, t, J=6.6 Hz), 3.46–3.52(1H, m), 3.65(3H, s), 3.84(1H, d, J=12.8 Hz), 3.92(1H, d, J=12.8 Hz), 4.22(2H, t, J=6.6 Hz), 6.79(2H, d, J=8.6 Hz), 7.02(2H, d, J=8.6 Hz), 7.39–7.46(3H, m), 7.97–8.02(2H, m).

Example 14

Methyl(S)-3-[4-[2-(5-methyl-2-phenyl-1,3-oxazol-4-yl)ethoxy]phenyl]-2-(4-chlorobenzylamino)propionate (Compound 14)

In the same manner as in Example 7, 116.4 mg of the title compound was obtained as colorless powder from 208.6 mg of Referential Compound 3 and 104.8 mg of 4-chlorobenzaldehyde.

IRν max(KBr): 3451, 3336, 3060, 3023, 2986, 2950, 2925, 2865, 1732, 1643, 1612, 1556, 1513, 1489, 1471, 1448, 1337, 1298, 1246, 1174, 1141, 1089, 1068, 1015, 819, 775, 715, 693 cm$^{-1}$.

$^1$H-NMR(CDCl$_3$)δ: 2.37(3H, s), 2.97(2H, t, J=6.8 Hz), 2.99(2H, brm), 3.52(1H, brm), 3.66–3.84(5H, m), 4.22(2H, t, J=6.8 Hz), 6.81(2H, d, J=8.6 Hz), 7.06(2H, d, J=8.6 Hz), 7.19–7.24(4H, m), 7.39–7.45(3H, m), 7.96–7.99(2H, m).

Example 15

Methyl(S)-3-[4-[2-(5-methyl-2-phenyl-1,3-oxazol-4-yl)ethoxy]phenyl]-2-(2-chlorobenzylamino)propionate (Compound 15)

In the same manner as in Example 7, 466.5 mg of the title compound was obtained as colorless oil from 609.3 mg of Referential Compound 3 and 230 µL of 2-chlorobenzaldehyde.

IRν max(neat): 3339, 3060, 2950, 1732, 1644, 1613, 1556, 1508, 1472, 1338, 1245, 1171, 1036, 948, 897, 831, 754, 716, 693 cm$^{-1}$.

$^1$H-NMR(CDCl$_3$)δ: 2.37(3H, s), 2.94–3.04(4H, m), 3.56 (1H, t, J=6.6 Hz), 3.64(3H, s), 3.85(1H, d, J=14.3 Hz), 3.96(1H, d, J=14.3 Hz), 4.21(2H, t, J=6.7 Hz), 6.81(2H, d, J=8.6 Hz), 7.07(2H, d, J=8.6 Hz), 7.15–7.21(2H, m), 7.27–7.31(1H, m), 7.32–7.45(4H, m), 7.94–7.99(2H, m).

Example 16

Methyl(S)-3-[4-[2-(5-methyl-2-phenyl-1,3-oxazol-4-yl)ethoxy]phenyl]-2-(4-bromobenzylamino)propionate (Compound 16)

In the same manner as in Example 7, 188.0 mg of the title compound was obtained as colorless powder from 208.6 mg Referential Compound 3 and 138.9 mg of 4-bromobenzaldehyde.

IRν max(KBr): 3339, 3060, 3023, 2949, 2921, 1733, 1646, 1609, 1557, 1509, 1488, 1246, 1172, 1135, 1011, 827, 693 cm$^{-1}$.

$^1$H-NMR(CDCl$_3$)δ: 2.38(3H, s), 2.93–3.00(4H, m), 3.49 (1H, t, J=6.6 Hz), 3.63(1H, d, J=13.4 Hz), 3.66(3H, s), 3.78(1H, d, J=13.4 Hz), 4.22(2H, t, J=6.6 Hz), 6.81(2H, d, J=8.6 Hz), 7.05(2H, d, J=8.6 Hz), 7.13(2H, d, J=8.4 Hz), 7.37–7.45(5H, m), 7.95–7.99(2H, m).

Example 17

Ethyl(S)-3-[4-[2-(5-methyl-2-phenyl-1,3-oxazol-4-yl)ethoxy]phenyl]-2-[N-(4-fluorobenzyl)-N-methylamino]propionate (Compound 17)

Under argon atmosphere, 60% sodium hydride (30 mg) was added at 0° C. to a solution of Compound 1 (253.8 mg) in tetrahydrofuran (5 mL), and the mixture was stirred for 30 minutes at room temperature. Under cooling with ice, methyl iodide (0.16 mL) was added thereto, and the resultant mixture was stirred for 88 hours at room temperature. Water was added to the reaction mixture, and the solvent was distilled off. The residue was subjected to extraction with ethyl acetate. The organic layer was washed with saturated brine and dried over anhydrous sodium sulfate. The solvent was removed under reduced pressure, and the resultant crude product was subjected to purification through silica gel column chromatography (ethyl acetate-hexane=1:4 to 1:2), to thereby yield 139.3 mg of the title compound as a colorless oil.

IRν max(neat): 3060, 2929, 1728, 1638, 1609, 1556, 1509, 1473, 1449, 1370, 1338, 1296, 1245, 1220, 1177, 1155, 1069, 1027, 948, 825, 775, 715, 693 cm$^{-1}$.

$^1$H-NMR(CDCl$_3$)δ: 1.23(3H, t, J=7.1 Hz), 2.28(3H, s), 2.37(3H, s), 2.87(1H, dd, J=13.7, 7.1 Hz), 2.97(2H, t, J=6.9 Hz), 2.97–3.06(1H, m), 3.48(1H, t, J=7.1 Hz), 3.56(1H, d, J=13.7 Hz), 3.75(1H, d, J=13.7 Hz), 4.07–4.19(2H, m), 4.22(2H, t, J=6.9 Hz), 6.80(2H, d, J=8.6 Hz), 6.91(2H, d, J=8.6 Hz), 7.04(2H, d, J=8.6 Hz), 7.11(2H, dd, J=8.6, 5.6 Hz), 7.37–7.45(3H, m), 7.95–8.00(2H, m).

Example 18

(S)-3-[4-[2-(5-Methyl-2-phenyl-1,3-oxazol-4-yl) ethoxy]phenyl]-2-(4-fluorobenzylamino)propionic Acid (Compound 18)

Compound 1 (1.88 g) was dissolved in ethanol (40 mL), and the solution was cooled to 0° C. A 10-%(w/v) aqueous sodium hydroxide solution (4.0 mL) was added thereto, and the mixture was stirred overnight, while the temperature of the mixture was allowed to rise spontaneously. Ethanol was evaporated, and the residue was diluted with water. Subsequently, 1.0-mol/L hydrochloric acid was added dropwise to the resultant solution, to thereby adjust the pH of the mixture to 5 to 6. The obtained crude product was washed with diethyl ether and water and dried, to thereby yield 1.58 g of the title compound as a colorless powder.

IRν max(KBr): 3422, 3060, 3014, 2949, 2921, 1610, 1514, 1423, 1395, 1330, 1250, 1181, 1023, 824 cm$^{-1}$.

$^1$H-NMR(DMSO-d$_6$)δ: 2.36(3H, s), 2.71–2.88(3H, m), 2.92(2H, t, J=6.6 Hz), 3.59(1H, d, J=13.7 Hz), 3.75(1H, d, J=13.7 Hz), 4.20(2H, t, J=6.6 Hz), 6.83(2H, d, J=8.4 Hz), 7.06–7.12(4H, m), 7.25(2H, dd, J=8.0, 5.6 Hz), 7.45–7.48 (3H, m), 7.85-7.92(2H, m).

m/z(ESI-): 473(M-H)$^-$.

mp.: 184.5–186.5° C.

$[α]_D^{27}$ (CH$_3$CO$_2$H): +21.3 (c=1.0)

Optical purity was determined through HPLC (CHIRALCEL OD-H (product of Daicel), 25° C., 1 mL/min, 279 nm, n-hexane/ethanol/trifluoroacetic acid=90/10/0.1, (R) compound: 8.19 min, (S) compound: 14.71 min) (98.64% ee).

Example 19

(S)-3-[4-[2-[2-(4-Fluorophenyl)-5-methyl-1,3-oxazol-4-yl]ethoxy]phenyl]-2-(4-fluorobenzylamino) propionic Acid (Compound 19)

In the same manner as in Example 18, 186.0 mg of the title compound was obtained as colorless powder from 224.9 mg of Compound 2.

IRν max(KBr): 3414, 3070, 2934, 2409, 1608, 1515, 1498, 1247, 1178, 1157, 1100, 1021, 843, 816, 742 cm$^{-1}$.

$^1$H-NMR(CD$_3$CO$_2$D)δ: 2.31(3H, s), 2.90–3.00(2H, m), 3.08–3.18(2H, m), 4.08–4.18(3H, m), 4.19–4.33(2H, m), 6.71(2H, d, J=8.3 Hz), 6.92–7.17(6H, m), 7.26–7.35(2H, m), 7.87–7.96(2H, m).

m/z(ESI-): 491(M-H)$^-$.

mp.: 191–193° C.

$[α]_D^{28}$(CH$_3$CO$_2$H): +32.6(c=0.20)

Example 20

(S)-3-[4-[2-[5-Methyl-2-(4-methylphenyl)-1,3-oxazol-4-yl]ethoxy]phenyl]-2-(4-fluorobenzylamino) propionic Acid (Compound 20)

In the same manner as in Example 18, 136.9 mg of the title compound was obtained as colorless powder from 188.0 mg of Compound 3.

IRν max(KBr): 3404, 3042, 2927, 2872, 2734, 2418, 1607, 1571, 1514, 1421, 1380, 1329, 1247, 1176, 1143, 1111, 1078, 1060, 1020, 898, 828, 769, 729, 642 cm$^{-1}$.

$^1$H-NMR(CD$_3$CO$_2$D)δ: 2.27(3H, s), 2.29(3H, s), 2.90–2.98(2H, m), 3.16–3.24(2H, m), 4.05–4.30(5H, m), 6.71(2H, d, J=8.1 Hz), 6.96(2H, dd, J=8.1, 8.1 Hz), 7.05(2H, d, J=7.4 Hz), 7.18(2H, d, J=8.1 Hz), 7.32–7.42(2H, m), 7.77(2H, d, J=8.1 Hz).

m/z(ESI-): 487(M-H)$^-$.

mp.: 196–198° C.

$[α]_D^{27}$(CH$_3$CO$_2$H): +19.3(c=0.23)

Example 21

(S)-3-[4-[2-[5-Methyl-2-(4-trifluoromethylphenyl)-1,3-oxazol-4-yl]ethoxy]phenyl]-2-(4-fluorobenzylamino)propionic Acid (Compound 21)

In the same manner as in Example 18, 204.2 mg of the title compound was obtained as colorless powder from 225.0 mg of Compound 4.

IRν max(KBr): 3393, 3042, 2937, 2734, 2637, 2409, 1617, 1514, 1414, 1388, 1326, 1248, 1167, 1124, 1082, 1064, 1015, 950, 899, 848, 820, 766, 714, 688, 670, 620 cm$^{-1}$.

$^1$H-NMR(CD$_3$CO$_2$D)δ: 2.35(3H, s), 2.93–3.02(2H, m), 3.18–3.37(2H, m), 4.10–4.36(5H, m), 6.71–6.78(2H, m), 6.95–7.05(2H, m), 7.06–7.19(2H, m), 7.36–7.52(2H, m), 7.70(2H, d, J=8.3 Hz), 8.07(2H, d, J=8.3 Hz).

m/z(ESI-): 541(M-H)$^-$.

mp.: 202–204° C.

$[α]_D^{28}$(CH$_3$CO$_2$H): +21.2(c=0.20)

Example 22

(S)-3-[4-[2-(5-Methyl-2-phenyl-1,3-thiazol-4-yl) ethoxy]phenyl]-2-(4-fluorobenzylamino)propionic Acid (Compound 22)

In the same manner as in Example 18, 134.7 mg of the title compound was obtained as colorless powder from 160.3 mg of Compound 5.

IRν max(KBr): 3423, 3057, 2920, 2864, 2548, 2409, 1595, 1513, 1422, 1339, 1305, 1247, 1180, 1113, 1021, 970, 874, 819, 762, 689 cm$^{-1}$.

$^1$H-NMR(CD$_3$CO$_2$D)δ: 2.46(3H, s), 3.20–3.32(4H, m), 4.20–4.35(5H, m), 6.72–6.79(2H, m), 6.96–7.06(2H, m), 7.07–7.15(2H, m), 7.38–7.49(5H, m), 7.85–7.92(2H, m).

m/z(ESI-): 489(M-H)$^-$.

mp.: 192–195° C.

$[α]_D^{28}$(CH$_3$CO$_2$H): +19.4(c=0.54)

Example 23

(S)-3-[4-[2-[5-Methyl-2-(morpholin-4-yl)-1,3-thiazol-4-yl]ethoxy]phenyl]-2-(4-fluorobenzylamino)propionic Acid (Compound 23)

In the same manner as in Example 18, 111.1 mg of the title compound was obtained as colorless powder from 147.3 mg of Compound 6.

IRν max(KBr): 3393, 2958, 2919, 2856, 2734, 2604, 2409, 1617, 1578, 1511, 1449, 1375, 1324, 1302, 1268, 1226, 1176, 1116, 1064, 1025, 941, 898, 819, 764, 714, 671, 630 cm$^{-1}$.

$^1$H-NMR(CD$_3$CO$_2$D)δ: 2.22(3H, s), 3.00–3.22(4H, m), 3.57–3.84(8H, m), 4.10–4.27(4H, m), 4.30(1H, d, J=12.8 Hz), 6.67–6.76(2H, m), 6.95–7.15(4H, m), 7.32–7.48(2H, m).

m/z(ESI−): 498(M−H)⁻.

mp.: 192–194° C.

$[\alpha]_D^{28}$ (CH$_3$CO$_2$H): +19.6(c=0.21)

Example 24

(S)-3-[4-[2-(5-Methyl-2-phenyl-1,3-oxazol-4-yl)ethoxy]phenyl]-2-(2-fluorobenzylamino)propionic Acid (Compound 24)

In the same manner as in Example 18, 75.8 mg of the title compound was obtained as colorless powder from 94.9 mg of Compound 7.

IRν max(KBr): 3414, 3060, 3033, 2930, 1618, 1513, 1459, 1423, 1386, 1339, 1302, 1249, 1181, 1107, 1069, 1023, 875, 827, 760, 692 cm⁻¹.

¹H-NMR(CD$_3$CO$_2$D)δ: 2.36(3H, s), 2.99(2H, t, J=6.2 Hz), 3.20(2H, d, J=5.1 Hz), 4.15(2H, t, J=6.2 Hz), 4.27(1H, d, J=12.7 Hz), 4.29(1H, t, J=5.1 Hz), 4.39(1H, d, J=12.7 Hz), 6.76(2H, d, J=7.7 Hz), 7.00–7.13(4H, m), 7.34–7.43(5H, m), 7.92–7.94(2H, m).

m/z(ESI−): 473(M−H)⁻.

mp.: 191–193° C.

$[\alpha]_D^{27}$ (CH$_3$CO$_2$H): +29.5(c=0.05).

Example 25

(S)-3-[4-[2-(5-Methyl-2-phenyl-1,3-oxazol-4-yl)ethoxy]phenyl]-2-(2,4-difluorobenzylamino)propionic Acid (Compound 25)

In the same manner as in Example 18, 208.8 mg of the title compound was obtained as colorless powder from 230.0 mg of Compound 8.

IRν max(KBr): 3385, 3042, 2927, 2871, 1603, 1512, 1432, 1388, 1339, 1281, 1250, 1180, 1142, 1101, 1068, 1021, 971, 846, 775, 715, 691 cm⁻¹.

¹H-NMR(DMSO-d$_6$)δ: 2.35(3H, s), 2.72-2.85(2H, m), 2.90(2H, t, J=6.4 Hz), 3.24–3.31(1H, m), 3.59(1H, d, J=14.0 Hz), 3.74(1H, d, J=14.0 Hz), 4.17(2H, t, J=6.4 Hz), 6.82(2H, d, J=8.2 Hz), 6.97(1H, dd, J=8.2, 8.2 Hz), 7.08(2H, d, J=8.2 Hz), 7.07–7.16(1H, m), 7.33(1H, ddd, J=8.2, 8.2, 8.2 Hz), 7.47–7.49(3H, m), 7.89–7.91(2H, m).

m/z(ESI−): 491(M−H)⁻.

mp.: 190–192° C.

$[\alpha]_D^{29}$(CH$_3$CO$_2$H): +43.5(c=0.21)

Example 26

(S)-3-[4-[2-(5-Methyl-2-phenyl-1,3-oxazol-4-yl)ethoxy]phenyl]-2-(3,4-difluorobenzylamino)propionic Acid (Compound 26)

In the same manner as in Example 18, 179.2 mg of the title compound was obtained as colorless powder from 211.0 mg of Compound 9.

IRν max(KBr): 3050, 2929, 2871, 1607, 1560, 1525, 1513, 1447, 1387, 1332, 1291, 1250, 1176, 1146, 1125, 1068, 1019, 816, 776, 718, 691, 627 cm⁻¹.

¹H-NMR(DMSO-d$_6$)δ: 2.35(3H, s), 2.73–2.82(2H, m), 2.90(2H, t, J=6.4 Hz), 3.18–3.21(1H, m), 3.56(1H, d, J=14.1 Hz), 3.75(1H, d, J=14.1 Hz), 4.17(2H, t, J=6.4 Hz), 6.83(2H, d, J=8.3 Hz), 7.00–7.08(1H, m), 7.09(2H, d, J=8.3 Hz), 7.15–7.30(2H, m), 7.47–7.49(3H, m), 7.89–7.91(2H, m).

m/z(ESI−): 491(M−H)⁻.

mp.: 202–204° C.

$[\alpha]_D^{29}$ (CH$_3$CO$_2$H): +44.2(c=0.10)

Example 27

(S)-3-[4-[2-(5-Methyl-2-phenyl-1,3-oxazol-4-yl)ethoxy]phenyl]-2-(2,3-difluorobenzylamino)propionic Acid (Compound 27)

In the same manner as in Example 18, 213.8 mg of the title compound was obtained as colorless powder from 250.0 mg of Compound 10.

IRν max(KBr): 3406, 3037, 2929, 2872, 2744, 2670, 2540, 2416, 1626, 1514, 1491, 1431, 1389, 1329, 1291, 1249, 1201, 1183, 1083, 1067, 1022, 832, 792, 736, 711, 691 cm⁻¹.

¹H-NMR(CD$_3$CO$_2$D)δ: 2.36(3H, s), 2.99(2H, t, J=6.0 Hz), 3.30(2H, d, J=5.8 Hz), 4.16(2H, t, J=6.0 Hz), 4.36(1H, t, J=5.8 Hz), 4.41(2H, s), 6.77(2H, d, J=8.2 Hz), 7.10–7.27(2H, m), 7.14(2H, d, J=8.2 Hz), 7.19–7.43(4H, m), 7.94–7.95(2H, m).

m/z(ESI−): 491(M−H)⁻.

mp.: 173–175° C.

$[\alpha]_D^{29}$(CH$_3$CO$_2$H): +27.0(c=1.1)

Example 28

(S)-3-[4-[2-(5-Methyl-2-phenyl-1,3-oxazol-4-yl)ethoxy]phenyl]-2-(2,6-difluorobenzylamino)propionic Acid (Compound 28)

In the same manner as in Example 18, 453.7 mg of the title compound was obtained as colorless powder from 530.4 mg of Compound 11.

IRν max(KBr): 3421, 3032, 2925, 2632, 1718, 1629, 1553, 1512, 1473, 1388, 1339, 1247, 1179, 1070, 1024, 826, 787, 717, 692 cm⁻¹.

¹H-NMR(CD$_3$CO$_2$D)δ: 2.49(3H, s), 3.14–3.25(2H, m), 3.33–3.54(2H, m), 4.25–4.37(2H, m), 4.40–4.58(3H, m), 6.85(2H, d, J=6.9 Hz), 6.94–7.05(2H, m), 7.25(2H, d, J=6.9 Hz), 7.40–7.52(1H, m), 7.53–7.66(3H, m), 8.16–8.24(2H, m).

m/z(ESI−): 491(M−H)⁻.

mp.: 165–167° C.

$[\alpha]_D^{29}$ (CH$_3$CO$_2$H): +39.5(c=0.21)

Example 29

(S)-3-[4-[2-(5-Methyl-2-phenyl-1,3-oxazol-4-yl)ethoxy]phenyl]-2-(2,4,6-trifluorobenzylamino)propionic Acid (Compound 29)

In the same manner as in Example 18, 189.1 mg of the title compound was obtained as colorless powder from 351.5 mg of Compound 12.

IRν max(KBr): 3174, 3016, 2933, 1610, 1555, 1510, 1449, 1340, 1243, 1211, 1184, 1123, 1082, 1009, 833, 772, 711, 688 cm⁻¹.

¹H-NMR(DMSO-d$_6$)δ: 2.34(3H, s), 2.71(1H, dd, J=13.6, 7.0 Hz), 2.78(1H, dd, J=13.6, 7.0 Hz), 2.90(2H, t, J=6.5 Hz), 3.26(1H, dd, J=7.0, 7.0 Hz), 3.61(1H, d, J=13.0 Hz), 3.71(1H, d, J=13.0 Hz), 4.16(2H, t, J=6.5 Hz), 6.79(2H, d, J=8.2 Hz), 7.04(2H, d, J=8.2 Hz), 7.10(2H, t, J=8.1 Hz), 7.47–7.49(3H, m), 7.89–7.91(2H, m)

m/z(ESI−): 509(M−H)⁻.

mp.: 168–170° C.

$[\alpha]_D^{29}$(CH$_3$CO$_2$H): +32.3(c=0.30)

Example 30

(S)-3-[4-[2-(5-Methyl-2-phenyl-1,3-oxazol-4-yl) ethoxy]phenyl]-2-(pentafluorobenzylamino) propionic Acid (Compound 30)

In the same manner as in Example 18, 328.4 mg of the title compound was obtained as colorless powder from 431.0 mg of Compound 13.

IRν max(KBr): 3395, 3060, 2941, 2874, 1609, 1509, 1448, 1336, 1296, 1248, 1178, 1137, 1068, 1015, 982, 937, 833, 773, 716, 689 cm$^{-1}$.

$^1$H-NMR(DMSO-d$_6$)δ: 2.35(3H, s), 2.60–2.70(1H, m), 2.72–2.82(1H, m), 2.90(2H, t, J=6.6 Hz), 3.18–3.22(1H, m), 3.71(1H, d, J=13.0 Hz), 3.80(1H, d, J=13.0 Hz), 4.15(2H, t, J=6.6 Hz), 6.77(2H, d, J=8.2 Hz), 7.04(2H, d, J=8.2 Hz), 7.47–7.52(3H, m), 7.87–7.94(2H, m).

m/z(ESI–): 545(M–H)$^-$.

mp.: 156–158° C.

[α]$_D^{29}$(CH$_3$CO$_2$H): +24.2(c=0.24)

Example 31

(S)-3-[4-[2-(5-Methyl-2-phenyl-1,3-oxazol-4-yl) ethoxy]phenyl]-2-(4-chlorobenzylamino)propionic Acid (Compound 31)

In the same manner as in Example 18, 73.7 mg of the title compound was obtained as colorless powder from 112.7 mg of Compound 14.

IRν max(KBr): 3423, 3060, 2930, 2865, 2735, 2642, 1609, 1513, 1491, 1448, 1386, 1333, 1249, 1181, 1107, 1088, 1061, 1013 cm$^-$.

$^1$H-NMR(CD$_3$CO$_2$D)δ: 2.35(3H, s), 2.98(2H, t, J=6.2 Hz), 3.13–3.17(2H, m), 4.11–4.17(3H, m), 4.35(2H, m), 6.74(2H, d, J=8.3 Hz), 7.61(2H, d, J=8.3 Hz), 7.28(4H, s), 7.39–7.42(3H, m), 7.90–7.94(2H, m).

m/z(ESI–) 489(M–H)$^-$, 491(M–H)$^-$.

mp.: 197–199° C.

[α]$_D^{26}$ (CH$_3$CO$_2$H): +44.0(c=0.06)

Example 32

(S)-3-[4-[2-(5-Methyl-2-phenyl-1,3-oxazol-4-yl) ethoxy]phenyl]-2-(2-chlorobenzylamino)propionic Acid (Compound 32)

In the same manner as in Example 18, 365.5 mg of the title compound was obtained as colorless powder from 406.5 mg of Compound 15.

IRν max(KBr): 3395, 3060, 3032, 2920, 2864, 1609, 1511, 1447, 1387, 1339, 1296, 1249, 1177, 1060, 1021, 830, 754, 716, 690 cm$^{-1}$.

$^1$H-NMR(CD$_3$CO$_2$D)δ: 2.35(3H, s), 2.99(2H, t, J=5.6 Hz), 3.26–3.35(2H, m), 4.17(2H, t, J=5.6 Hz), 4.30–4.52 (3H, m), 6.78(2H, d, J=7.7 Hz), 7.14(2H, d, J=7.7 Hz), 7.21–7.37(3H, m), 7.38–7.45(3H, m), 7.59–7.70(1H, m), 7.90–7.98(2H, m).

m/z(ESI–): 489(M–H)$^-$, 491(M–H)$^-$.

mp.: 143–145° C.

[α]$_D^{29}$(CH$_3$CO$_2$H): +15.1(c=0.21)

Example 33

(S)-3-[4-[2-(5-Methyl-2-phenyl-1,3-oxazol-4-yl) ethoxy]phenyl]-2-(4-bromobenzylamino)propionic Acid (Compound 33)

In the same manner as in Example 18, 152.3 mg of the title compound was obtained as colorless powder from 185.9 mg of Compound 16.

IRν max(KBr): 3423, 3051, 2931, 2865, 1608, 1513, 1490, 1451, 1388, 1333, 1249, 1178, 1070, 1016, 837, 799, 716, 691 cm$^{-1}$.

$^1$H-NMR(CD$_3$CO$_2$D)δ: 2.35(3H, s), 2.98(2H, t, J=6.1 Hz), 3.12–3.16(2H, m), 4.09–4.16(3H, m), 4.24(1H, t, J=5.9 Hz), 4.31(1H, d, J=13.4 Hz), 6.74(2H, d, J=8.4 Hz), 7.05 (2H, d, J=8.4 Hz), 7.22(2H, d, J=8.4 Hz), 7.39–7.44(5H, m), 7.90–7.93(2H, m).

m/z(ESI–): 533(M–H)$^-$, 535(M–H)$^-$.

mp.: 196–199° C.

[α]$_D^{27}$ (CH$_3$CO$_2$H): +35.5(c=0.09)

Example 34

(S)-3-[4-[2-(5-Methyl-2-phenyl-1,3-oxazol-4-yl) ethoxy]phenyl]-2-[N-(4-fluorobenzyl)-N-methylamino]propionic Acid (Compound 34)

In the same manner as in Example 18, 105.6 mg of the title compound was obtained as colorless powder from 163.3 mg of Compound 17.

IRν max(KBr): 3422, 3042, 2923, 2237, 1609, 1510, 1449, 1351, 1285, 1246, 1225, 1175, 1108, 1018, 855, 828, 765, 714, 691, 647 cm$^{-1}$.

$^1$H-NMR(DMSO-d$_6$)δ: 2.18(3H, s), 2.36(3H, s), 2.79(1H, dd, J=13.7, 7.7 Hz), 2.88–2.97(3H, m), 3.32–3.45(1H, m), 3.55(1H, d, J=13.3 Hz), 3.71(1H, d, J=13.3 Hz), 4.19(2H, t, J=6.4 Hz), 6.83(2H, d, J=8.4 Hz), 7.01(2H, d, J=8.4 Hz), 7.05–7.15(4H, m), 7.45–7.52(3H, m), 7.88–7.93(2H, m).

m/z(ESI–): 487(M–H)$^-$.

mp.: 142–145° C.

[α]$_D^{32}$(CH$_3$OH): +13.6(c=0.58)

Example 35

Sodium (S)-3-[4-[2-(5-methyl-2-phenyl-1,3-oxazol-4-yl)ethoxy]phenyl]-2-(4-fluorobenzylamino) propionate (Compound 35)

Compound 18 (1.57 g) was suspended in methanol (30 mL), and sodium methoxide was added to the resultant mixture until an substantially homogeneous solution was obtained. The solution was filtered, and the filtrate was concentrated. Diethyl ether was added thereto, and the resultant colorless crystals were collected through filtration and dried under reduced pressure, to thereby yield 1.57 g of the title compound.

IRν max(KBr): 3422, 3060, 3033, 2921, 2865, 1590, 1510, 1451, 1398, 1339, 1247, 1172, 1116, 1023, 824 cm$^{-1}$.

$^1$H-NMR(DMSO-d$_6$)δ: 2.36(3H, s), 2.75–2.86(3H, m), 2.91(2H, t, J=6.6 Hz), 3.35(1H, d, J=13.5 Hz), 3.55(1H, d, J=13.5 Hz), 4.17(2H, t, J=6.6 Hz), 6.77(2H, d, J=8.3 Hz), 7.00–7.20(6H, m), 7.45–7.51(3H, m), 7.88–7.93(2H, m).

m/z(ESI–): 473(M–Na)$^-$.

mp.: 179–181° C.

[α]$_D^{30}$(CH$_3$OH): +7.7(c=1.1)

Example 36

(S)-3-[4-[2-(5-Methyl-2-phenyl-1,3-oxazol-4-yl) ethoxy]phenyl]-2-(4-fluorobenzylamino)propionic Acid Hydrochloride (Compound 36)

Under argon atmosphere, hydrogen chloride gas was introduced into a solution of Referential Compound 2 (187.4 mg) in ethyl acetate (3 mL) for 0.5 hours at 0° C. The solvent was removed under reduced pressure, and the resultant crude product was washed with diethyl ether and dried under reduced pressure, to thereby yield 142.6 mg of the title compound as a colorless amorphous compound.

IRν max(KBr): 3386, 2930, 2775, 1736, 1677, 1608, 1513, 1438, 1376, 1248, 1227, 1181, 1028, 953, 837, 778, 715, 687 cm$^{-1}$.

$^1$H-NMR(DMSO-d$_6$)δ: 2.35(3H, s), 2.91(2H, t, J=6.6 Hz), 3.03(1H, dd, J=14.1, 8.4 Hz), 3.30(1H, dd, J=14.1, 4.3 Hz), 4.05–4.16(3H, m), 4.18(2H, t, J=6.6 Hz), 6.89(2H, d, J=8.5 Hz), 7.15(2H, d, J=8.5 Hz), 7.24(1H, d, J=8.6 Hz), 7.27(1H, d, J=8.6 Hz), 7.47–7.49(3H, m), 7.55(1H, d, J=8.6 Hz), 7.57(1H, d, J=8.6 Hz), 7.89–7.92(2H, m)

m/z(ESI−): 473(M−HCl−H)$^-$.

mp.: 198–200° C.

$[\alpha]_D^{29}$ (CH$_3$CO$_2$H): +39.9(c=0.26)

Example 37

Ethyl(S)-3-[4-[2-(5-methyl-2-phenyl-1,3-oxazol-4-yl)ethoxy]phenyl]-2-(4-fluorobenzylamino)propionate Hydrochloride (Compound 37)

Compound 1 (256 mg) was dissolved in diethyl ether (5.0 mL), and a 1,4-dioxane solution saturated with hydrogen chloride (0.3 mL) was added thereto, followed by stirring. The produced colorless crystals were collected through filtration and dried under reduced pressure, to thereby yield 126 mg of the title compound.

IRν max(KBr): 3421, 2930, 2727, 1736, 1608, 1513, 1473, 1448, 1396, 1376, 1300, 1248, 1226, 1179, 1162, 1026, 835 cm$^{-1}$.

$^1$H-NMR(CDCl$_3$)δ: 1.17(3H, t, J=6.8 Hz), 2.46(3H, s), 3.15(2H, t, J=6.0 Hz), 3.35–3.51(2H, m), 3.82(1H, brs), 4.08–4.31(6H, m), 6.78(2H, d, J=8.5 Hz), 7.02(2H, dd, J=8.5, 8.5 Hz), 7.12(2H, d, J=8.5 Hz), 7.51–7.61(5H, m), 8.26(2H, d, J=8.5 Hz).

m/z(ESI+): 503(M−HCl+H)$^+$.

mp.: 69–71° C.

$[\alpha]_D^{26}$ (CHCl$_3$): +18.2(c=0.50)

Example 38

Ethyl(S)-3-[4-[2-(5-methyl-2-phenyl-1,3-oxazol-4-yl)ethoxy]phenyl]-2-(4-fluorobenzylamino)propionate methanesulfonate (Compound 38)

Methanesulfonic acid (7.8 mL) was added to a solution of Compound 1 (50.2 g) in ethanol (150 mL), and the temperature of the solution was elevated to 40° C. The solution was stirred for 10 minutes, and the reactor was cooled in an ice bath. When the interior temperature reached 10° C. or lower, diisopropyl ether (300 mL) was added thereto, and the mixture was left to stand for night and day in a dark cold place. The product was collected through filtration with a glass filter and dried under reduced pressure, to thereby yield 52.1 g of the title compound as colorless crystals.

IRν max(KBr): 3423, 2957, 2759, 2627, 1742, 1637, 1607, 1224, 1156, 1040 cm$^{-1}$.

$^1$H-NMR(CDCl$_3$)δ: 0.98(3H, t, J=7.2 Hz), 2.30(3H, s), 2.35(3H, s), 2.88–3.95(4H, m), 3.99(2H, q, J=7.2 Hz), 4.17–4.21(5H, m), 6.90(2H, d, J=8.4 Hz), 7.10(2H, d, J=8.4 Hz), 7.28(2H, dd, J=8.7, 8.7 Hz), 7.47–7.54(5H, m), 7.88–7.91(2H, m).

m/z(ESI+): 503(M−CH$_3$SO$_3$H+H)$^+$.

mp.: 144° C.

$[\alpha]_D^{20}$(C$_2$H$_5$OH): +24.3(c=1.3).

Comparative Example 1

(S)-3-[4-[2-(5-Methyl-2-phenyl-1,3-oxazol-4-yl)ethoxy]phenyl]-2-(benzylamino)propionic Acid (the Compound Described in Example 27 of WO96/38415, Comparative Compound 1)

Ethyl(S)-3-[4-[2-(5-methyl-2-phenyl-1,3-oxazol-4-yl)ethoxy]phenyl]-2-(benzylamino)propionate was synthesized through the method described in WO96/38415, and the product (745 mg) was processed, to thereby yield 507 mg of the title compound as a colorless powder.

IRν max(KBr): 3422, 3035, 2953, 2870, 1617, 1511, 1438, 1389, 1334, 1304, 1247, 1180, 1143, 1113, 1068 cm$^{-1}$.
$^1$H-NMR(CD$_3$OD)δ: 2.36(3H, s), 2.99(2H, t, J=6.1 Hz), 3.11–3.22(2H, m), 4.11–4.16(3H, m), 4.23(1H, t, J=6.3 Hz), 4.32(1H, d, J=12.7 Hz), 6.76(2H, d, J=8.1 Hz), 7.07(2H, d, J=8.1 Hz), 7.30–7.42(8H, m), 7.92–7.93(2H, m).

m/z(ESI−): 455(M−H)$^-$.

mp.: 206–209° C.

$[\alpha]_D^{29}$(CH$_3$CO$_2$H): +15.5(c=0.49)

Test Example

Blood glucose Lowering Effect and Blood Lipid (Blood TG and Blood FFA) Lowering Effect in Mice Each of the test compounds was suspended in a 0.5-% (w/v) sodium CMC solution, and the suspension was forcedly administered via oral route once a day over seven days to male KKA$^y$ mice (obesity/noninsulin-dependent diabetes mellitus model, 6 to 7 weeks old, 3 to 5 animals per group) (1 mg/kg/day). During this 7-day period, feed and water were taken ad libitum. On the day following the final administration, blood was drawn from the tail vein without anesthesia and centrifuged, to thereby prepare plasma samples. Plasma glucose level, plasma TG level, and plasma FFA level of the samples were determined through the enzymatic method by use of an L-type Wako Glu2 (Wako Pure Chemical Industries), an L-type Wako TG-H (Wako Pure Chemical Industries), and an NEFA-HA Test Wako (Wako Pure Chemical Industries), respectively, by means of a full-automated clinical chemistry analyzer (CL-8000, Shimadzu Corporation). Percent reduction was determined from the obtained values by use of the following equations. The results are shown in Table 1.

TABLE 1

| Compound | Percent reduction of blood glucose level (%) | Percent reduction of blood TG level (%) | Percent reduction of blood FFA level (%) |
|---|---|---|---|
| Compound 18 | 15 | 40 | 27 |
| Compound 20 | 21 | 36 | 25 |
| Compound 22 | 33 | 53 | 36 |
| Compound 27 | 40 | 48 | 16 |
| Compound 28 | 50 | 65 | 54 |
| Compound 29 | 43 | 74 | 58 |
| Compound 32 | 39 | 33 | 13 |
| Compound 35 | 36 | 47 | 33 |

TABLE 1-continued

| Compound | Percent reduction of blood glucose level (%) | Percent reduction of blood TG level (%) | Percent reduction of blood FFA level (%) |
|---|---|---|---|
| Compound 38 | 25 | 33 | 16 |
| Comparative Compound 1 | 12 | 17 | −2 |

Percent reduction of blood glucose level (%) = [(Blood glucose level of the control group − Blood glucose level of the group to which a test compound is administered)/Blood glucose level of the control group] × 100
Percent reduction of blood TG level (%) = [(Blood TG level of the control group − Blood TG level of the group to which a test compound is administered)/Blood TG level of the control group] × 100
Percent reduction of blood FFA level (%) = [(Blood FFA level of the control group − Blood FFA level of the group to which a test compound is administered)/Blood FFA level of the control group] × 100

As shown in Table 1, the present compound (1) or a salt thereof was found to exhibit not only a blood glucose level lowering effect, but also remarkably excellent effect of lowering blood lipid (TG and FFA) levels as compared with the compound described in Example 27 of WO96/38415.

Separately, the present compound (1) or a salt thereof was orally administered to KKA$^y$ mice over two weeks (0.1, 0.3, or 1 mg/kg/day), and plasma adiponectin level of each mouse was determined. Compound 18 was found to exhibit particularly excellent effect of increasing plasma adiponectin level, indicating that Compound 18 exerts antidiabete and antiarteriosclerosis effects.

Industrial Applicability

The present invention provides a drug which exhibits potent blood glucose lowering effect and blood lipid lowering effect, and the drug is particularly useful as a preventive or therapeutic agent for diabetes, hyperlipidemia, impaired glucose tolerance, arteriosclerosis, or similar pathological conditions.

What is claimed is:

1. A halogenobenzylaminopropionic acid derivative represented by the following formula (1):

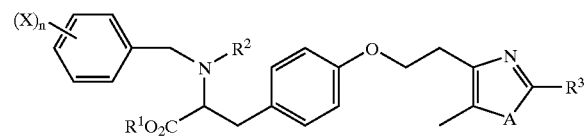

(1)

wherein each of $R^1$ and $R^2$, which may be identical to or different from each other, represents a hydrogen atom or a lower alkyl group; $R^3$ represents a phenyl group which may have a substituent, a morpholinyl group, or a pyridinyl group; X represents a halogen atom; n represents an integer of 1 to 5; and A represents an oxygen atom or a sulfur atom; or a pharmaceutically acceptable salt of the derivative.

2. A halogenobenzylaminopropionic acid derivative as described in claim 1, wherein $R^1$ is a hydrogen atom, a methyl group, or an ethyl group, $R^2$ is a hydrogen atom or a methyl group, $R^3$ is a morpholinyl group or a phenyl group which may have a substituent, X is a fluorine atom, a chlorine atom, or an bromine atom, and n is an integer of 1 to 3; or a pharmaceutically acceptable salt of the derivative.

3. A halogenobenzylaminopropionic acid derivative as described in claim 2, wherein $R^3$ is a phenyl group which may have a substituent and X is a fluorine atom or a chlorine atom; or a pharmaceutically acceptable salt of the derivative.

4. A halogenobenzylaminopropionic acid derivative selected from the group consisting of ethyl(S)-3-[4-[2-(5-methyl-2-phenyl-1,3-oxazol-4-yl)ethoxy]phenyl]-2-(4-fluorobenzylamino)propionate, (S)-3-[4-[2-(5-methyl-2-phenyl-1,3-oxazol-4-yl)ethoxy]phenyl]-2-(4-fluorobenzylamino)propionic acid, (S)-3-[4-[2-[5-methyl-2-(4-methylphenyl)-1,3-oxazol-4-yl]ethoxy]phenyl]-2-(4-fluorobenzylamino)propionic acid, (S)-3-[4-[2-(5-methyl-2-phenyl-1,3-thiazol-4-yl)ethoxy]phenyl]-2-(4-fluorobenzylamino)propionic acid, (S)-3-[4-[2-[5-methyl-2-(morpholin-4-yl)-1,3-thiazol-4-yl]ethoxy]phenyl]-2-(4-fluorobenzylamino)propionic acid, (S)-3-[4-[2-(5-methyl-2-phenyl-1,3-oxazol-4-yl)ethoxy]phenyl]-2-(2,3-difluorobenzylamino)propionic acid, (S)-3-[4-[2-(5-methyl-2-phenyl-1,3-oxazol-4-yl)ethoxy]phenyl]-2-(2,6-difluorobenzylamino)propionic acid, (S)-3-[4-[2-(5-methyl-2-phenyl-1,3-oxazol-4-yl)ethoxy]phenyl]-2-(2,4,6-trifluorobenzylamino)propionic acid, (S)-3-[4-[2-(5-methyl-2-phenyl-1,3-oxazol-4-yl)ethoxy]phenyl]-2-(4-chlorobenzylamino)propionic acid, (S)-3-[4-[2-(5-methyl-2-phenyl-1,3-oxazol-4-yl)ethoxy]phenyl]-2-(2-chlorobenzylamino)propionic acid, and (S)-3-[4-[2-(5-methyl-2-phenyl-1,3-oxazol-4-yl)ethoxy]phenyl]-2-[N-(4-fluorobenzyl)-N-methylamino]propionic acid; or a pharmaceutically acceptable salt of the derivative.

5. A drug composition comprising a halogenobenzylaminopropionic acid derivative or a pharmaceutically acceptable salt of the derivative as recited in any of claim 1, and a pharmaceutically acceptable carrier.

6. A method for treating diabetes and/or hyperlipidemia, which comprises administering, to a subject in need thereof, an effective dose of a halogenobenzylaminopropionic acid derivative or a pharmaceutically acceptable salt of the derivative as recited in claim 1.

7. A method of increasing the plasma adiponectin level which comprises administering, to a subject in need thereof, an effective dose of ethyl (S)-3-[4-[2-(5-methyl-2-phenyl-1,3-oxazol-4yl)ethoxyl]phenyl]-2-(4-fluorobenzylamino) propionate acid, or a pharmaceutically acceptable salt thereof.

8. A method for treating diabetes and/or hyperlipidemia caused by diabetes, which comprises administering, to a subject in need of thereof, an effective dose of a halogenobenzylaminopropionic acid derivative or a pharmaceutically acceptable salt of the derivative as recited in claim 1.

* * * * *